(12) United States Patent
Pai et al.

(10) Patent No.: US 6,242,199 B1
(45) Date of Patent: Jun. 5, 2001

(54) ASSAYS FOR GROWTH HORMONE SECRETAGOGUE RECEPTORS

(75) Inventors: Lee-Yuh Pai, Westfield; Scott D. Feighner, Highlands; Andrew D. Howard, Park Ridge; Sheng-Shung Pong, Edison; Leonardus H. T. Van Der Ploeg, Scotch Plains, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/077,675

(22) PCT Filed: Dec. 10, 1996

(86) PCT No.: PCT/US96/19442

§ 371 Date: Jun. 3, 1998

§ 102(e) Date: Jun. 3, 1998

(87) PCT Pub. No.: WO97/22004

PCT Pub. Date: Jun. 19, 1997

Related U.S. Application Data

(60) Provisional application No. 60/019,259, filed on Jun. 6, 1996, and provisional application No. 60/008,584, filed on Dec. 13, 1995.

(51) Int. Cl.[7] .................................................. G01N 33/566
(52) U.S. Cl. .................. 435/7.2; 435/7.21; 435/7.72; 435/69.1; 530/350; 536/23.1; 536/23.5
(58) Field of Search .................................... 435/7.2, 7.21, 435/66, 7.72, 69.1; 436/501; 530/350, 399, 300; 536/23.1, 23.5

(56) References Cited

U.S. PATENT DOCUMENTS

| | | | |
|---|---|---|---|
| 3,239,345 | 3/1966 | Hodge et al. | 99/2 |
| 4,036,979 | 7/1977 | Asato | 424/275 |
| 4,410,513 | 10/1983 | Momany | 424/177 |
| 4,411,890 | 10/1983 | Momany | 424/177 |
| 5,057,417 | 10/1991 | Hammonds | 435/69.1 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |
| 5,374,721 | 12/1994 | Schoen et al. | 540/491 |
| 5,430,144 | 7/1995 | Schoen et al. | 540/461 |
| 5,434,261 | 7/1995 | Schoen et al. | 540/461 |
| 5,438,136 | 8/1995 | Devita et al. | 564/456 |
| 5,492,916 | 2/1996 | Morriello et al. | 514/318 |
| 5,494,919 | 2/1996 | Morriello et al. | 514/323 |
| 5,494,920 | 2/1996 | Chen et al. | 514/323 |
| 5,583,010 | 12/1996 | Baumbach et al. | 435/69.1 |
| 5,591,641 | 1/1997 | Thorner et al. | 435/69.1 |
| 5,830,433 | * 11/1999 | Dean et al. | 424/1.81 |

FOREIGN PATENT DOCUMENTS

| | | |
|---|---|---|
| 0144230 | 12/1984 | (EP) . |
| 0513974 | 3/1992 | (EP) . |
| WO 89/07110 | 8/1989 | (WO) . |
| WO 89/07111 | 8/1989 | (WO) . |
| WO 89/04081 | 3/1993 | (WO) . |
| WO 94/07486 | 4/1994 | (WO) . |
| WO 94/08583 | 4/1994 | (WO) . |
| WO 94/11012 | 5/1994 | (WO) . |
| WO 94/13696 | 6/1994 | (WO) . |
| WO 94/19367 | 9/1994 | (WO) . |
| WO 95/03289 | 2/1995 | (WO) . |
| WO 95/03290 | 2/1995 | (WO) . |
| WO 95/09633 | 4/1995 | (WO) . |
| WO 95/11029 | 4/1995 | (WO) . |
| WO 95/12598 | 5/1995 | (WO) . |
| WO 95/13069 | 5/1995 | (WO) . |
| WO 95/14666 | 6/1995 | (WO) . |
| WO 95/16675 | 6/1995 | (WO) . |
| WO 95/16692 | 6/1995 | (WO) . |
| WO 95/17422 | 6/1995 | (WO) . |
| WO 95/17423 | 6/1995 | (WO) . |
| WO 95/34311 | 12/1995 | (WO) . |
| WO 96/02530 | 2/1996 | (WO) . |

OTHER PUBLICATIONS

Cubitt et al., "Understanding, improving & using green fluorescent proteins" Trends Biochem Sci., vol. 20, pp. 4480–455, 1995.

Julius et al., "Molecular Characterization of a Functional cDNA Encoding the Serotonin 1c Receptor" Science, vol. 241, pp. 558–564, 1988.

King et al., "Control of Yeast Mating . . . Subunit" Science, vol. 250, pp. 121–123, 1990.

Ok, et al., "Structure–Activity Relationships of the Non–peptidyl Growth Hormond Secretagogue L–692, 429", Bioorg. & Med. Chem. Letters, vol. 4, No. 22, pp. 2709–2719 1994.

Patchett, et al., "Design and biological activities of L–163, 191 (MK–0677): A potent, orally active growth hormond secretagogue", Proc. Natl. Acad. Sci. USA, vol. 92, pp. 7001–7005, Jul. 1995.

Schoen, et al., "Section IV: Immunology, Endocrinology and Metaboles", Ann. Rep. in Med. Chem., vol. 28, pp. 177–183 (1993).

Smith, et al., "A Nonpeptidyl Growth Hormone Secretagogue", Science, vol. 260, pp. 1640–1643, Jun. 11, 1993.

Aloi, et al., J. of Clin. End. and Met., vol. 79, No. 4, pp. 943–949, 1994.

(List continued on next page.)

Primary Examiner—Elizabeth Kemmerer
Assistant Examiner—Claire M. Kaufman
(74) Attorney, Agent, or Firm—Anna L. Cocuzzo; Jack L. Tribble

(57) ABSTRACT

An assay for the detection of growth hormone secretagogue receptors and growth hormone secretagogue related receptors is described. As these receptors are a member of the G protein coupled receptors, a subunit of the G protein must be present in order for expression to be detected. A similar assay is described where the presence of growth hormone secretagogues are detected.

8 Claims, 34 Drawing Sheets

OTHER PUBLICATIONS

Bowers, et al., J. of Clin. End. and Met., vol. 79, No. 4, pp. 940–942, 1994.

Williams, R.H., Textbook of Endocrinology, 5th edition, W.B. Saunders Company: Philadelphia, PA, pp790–791, 1974.*

Wu et al., Activation of phospholipase C by alpha1–adrenergice receptors is mediated by the alpha subunits of Gq family, J. Biol. Chem., 267 (36): 25798–25802 (Dec. 1992).*

Ganong, W.F., Review of Medical Physiology, Appleton & Lange:Norwalk, CT, pp. 373–374, 1995.*

* cited by examiner

```
              10        20        30        40
              .         .         .         .
       CCTCACGCTGCCAGACCTGGGCTGGGACGCTCCCCCTGAA     40
       AACGACTCGCTAGTGGAGGAGCTGCTGCCGCTCTTCCCCA     80
       CGCCGCTGTTGGCGGGCGTCACCGCCACCTGCGTGGCGCT    120
       CTTCGTGGTGGGTATCGCGGGCAACCTGCTCACGATGCTG    160
       GTAGTGTCACGCTTCCGCGAGATGCGCACCACCACCAACC    200

210       220       230       240
              .         .         .         .
       TCTACCTGTCCAGCATGGCCTTCTCCGACCTACTCATCTT    240
       CCTCTGCATGCCCCTCGACCTCTTCCGCCTCTGGCAGTAC    280
       CGGCCTTGGAACCTTGGCAACCTGCTCTGCAAACTCTTCC    320
       AGTTCGTTAGCGAGAGCTGCACCTACGCCACAGTGCTCAC    360
       CATCACCGCGCTGAGCGTCGAGCGCTACTTCGCCATCTGC    400

410       420       430       440
              .         .         .         .
       TTCCCGCTGCGGGCCAAGGTAGTGGTCACCAAGGGCCGGG    440
       TAAAGCTGGTCATCCTGGTCATCTGGGCCGTGGCCTTCTG    480
       CAGCGCCGGGCCCATCTTCGTGCTGGTCGGAGTGGAGCAT    520
       GATAACGGCACTGACCCTCGGGACACCAACGAGTGCCGCG    560
       CCACGGAGTTCGCCGTGCGCTCCGGGCTGCTTACCGTCAT    600

610       620       630       640
              .         .         .         .
       GGTCTGGGTGTCCAGTGTCTTCTTCTTCCTGCCTGTCTTC    640
       TGCCTCACTGTGCTCTATAGCCTCATCGGCAGGAAGCTCT    680
       GGCGGAGGAAGCGCGGCGAGGCGGCGGTGGGCTCCTCGCT    720
       CAGGGACCAGAACCACAAACAAACCGTGAAAATGCTGGCT    760
       GTAGTGGTGTTTGCTTTCATACTCTGCTGGCTGCCTTTCC    800

810       820       830       840
              .         .         .         .
       ATGTAGGGCGATATTTATTTTCCAAATCCTTGGAGCCTGG    840
       CTCTGTGGAGATTGCTCAGATCAGCCAATACTGCAACCTC    880
       GTGTCCTTTGTCCTCTTCTACCTCAGTGCGGCCATCAACC    920
       CTATTCTGTACAACATCATGTCCAAGAAGTATCGGGTGGC    960
       GGTGTTCAAACTGCTGGGATTTGAGCCCTTCTCACAGAGG   1000

1010      1020      1030      1040
              .         .         .         .
       AAACTCTCCACTCTGAAGGATGAAAGTTCTCGGGCCTGGA   1040
       CAGAATCTAGTATTAATACATGA   1063
```

FIG. 1

```
              10         20
MLVVSRFREM  RTTTNLYLSS    20
MAFSDLLIFL  CMPLDLFRLW    40
QYRPWNLGNL  LCKLFQFVSE    60
SCTYATVLTI  TALSVERYFA    80
ICFPLRAKVV  VTKGRVKLVI   100

110        120
LVIWAVAFCS  AGPIFVLVGV   120
EHDNGTDPRD  TNECRATEFA   140
VRSGLLTVMV  WVSSVFFFLP   160
VFCLTVLYSL  IGRKLWRRKR   180
GEAAVGSSLR  DQNHKQTVKM   200

210        220
LAVVVFAFIL  CWLPFHVGRY   220
LFSKSLEPGS  VEIAQISQYC   240
NLVSFVLFYL  SAAINPILYN   260
IMSKKYRVAV  FKLLGFEPFS   280
QRKLSTLKDE  SSRAWTESSI   300

```
1                                    30
LTLPDLGWDA  PPENDSLVEE  LLPLFPTRLL

HELIX 1                           60
AGVTATCVAL  FVVGIAGNLL  TMLVVSRFRE

HELIX 2                     90
MRTTTNLYLS  SMAFSDLLIF  ICMPLDLFRL

HELIX 3    120
WQYRPWNLGN  LLCKLFQFVS  ESCTYATVLT

150
ITALSVERYF  AICFPLRAKV  VVTKGRVKLV

HELIX 4                          180
ILVIWAVAFC  SAGPIFVLVG  VEHDNGTDPR

210
DTNECRATEF  AVRSGLLTVM  VWVSSVFFFL

HELIX 5                             240
PVFCLTVLYS  LIGRKLWRRK  RGEAAVGSSL

HELIX 6           270
RDQNHKQTVK  MLAVVVFAFI  LCWLPFHVGR

300
YLFSKSLEPG  SVEIAQISQY  CNLVSFVLFY

HELIX 7                             330
LSAAINPILY  NIMSKKYRVA  VFKLLGFEPF

353
SQRKLSTLKD  ESSRAWTESS  INT
```

FIG.3

```
              10        20        30        40
              .         .         .         .
     GCAGCCTCTCACTTCCCTCTTTCCTCTCCTAGCATCCTCC    40
     CTGAGAGCCCGCGCTCGATACTCCTTTGCACTCTTTCGCG    80
     CCTAAGAGAACCTTCTCTGGGACCAGCCGGCTCCACCCTC   120
     TCGGTCCTATCCAAGAGCCAGTTAAGCAGAGCCCTAAGCA   160
     TGTGGAACGCGACCCCGAGCGAGGAACCGGGGCCCAACCT   200

210       220       230       240
              .         .         .         .
     CACGCTGCCAGACCTGGGCTGGGACGCTCCCCCTGAAAAC   240
     GACTCGCTAGTGGAGGAGCTGCTGCCGCTCTTCCCCACGC   280
     CGCTGTTGGCGGGCGTCACCGCCACCTGCGTGGCGCTCTT   320
     CGTGGTGGGTATCGCGGGCAACCTGCTCACGATGCTGGTA   360
     GTGTCACGCTTCCGCGAGATGCGCACCACCACCAACCTCT   400

410       420       430       440
              .         .         .         .
     ACCTGTCCAGCATGGCCTTCTCCGACCTACTCATCTTCCT   440
     CTGCATGCCCCTCGACCTCTTCCGCCTTTGGCAGTACCGG   480
     CCTTGGAACCTTGGCAACCTGCTCTGCAAACTCTTCCAGT   520
     TCGTTAGCGAGAGCTGCACCTACGCCACAGTGCTCACCAT   560
     CACCGCGCTGAGCGTCGAGCGCTACTTCGCCATCTGCTTC   600

610       620       630       640
              .         .         .         .
     CCGCTGCGGGCCAAGGTAGTGGTCACCAAGGGCCGGGTAA   640
     AGCTGGTCATCCTGGTCATCTGGGCCGTGGCCTTCTGCAG   680
     CGCCGGGCCCATCTTCGTGCTGGTCGGAGTGGAGCATGAT   720
     AACGGCACTGACCCTCGGGACACCAACGAGTGCCGCGCCA   760
     CGGAGTTCGCCGTGCGCTCCGGGCTGCTTACCGTCATGGT   800

810       820       830       840
              .         .         .         .
     CTGGGTGTCCAGTGTCTTCTTCTTCCTGCCTGTCTTCTGC   840
     CTCACTGTGCTCTATAGCCTCATCGGCAGGAAGCTCTGGC   880
     GGAGGAAGCGCGGCGAGGCGGCGGTGGGCTCCTCGCTCAG   920
     GGACCAGAACCACAAACAAACCGTGAAAATGCTGGGTGGG   960
     TCTCAATGCGCCCTCGAGCTTTCTCTCCCGGGTCCCCTCC  1000

1010      1020      1030      1040
              .         .         .         .
     ACTCCTCGTGCCTTTTCTCTTCTCCCTGA  1029
```

FIG.4

```
              10         20         30         40
              .          .          .          .
    MWNATPSEEP GPNLTLPDLG WDAPPENDSL VEELLPLFPT   40
    PLLAGVTATC VALFVVGIAG NLLTMLVVSR FREMRTTTNL   80
    YLSSMAFSDL LIFLCMPLDL FRLWQYRPWN LGNLLCKLFQ  120
    FVSESCTYAT VLTITALSVE RYFAICFPLR AKVVVTKGRV  160
    KLVILVIWAV AFCSAGPIFV LVGVEHDNGT DPRDTNECRA  200

210        220        230        240
              .          .          .          .
    TEFAVRSGLL TVMVWVSSVF FFLPVFCLTV LYSLIGRKLW  240
    RRKRGEAAVG SSLRDQNHKQ TVKMLGGSQC ALELSLPGPL  280
    HSSCLFSSP  289
```

FIG. 5

```
          10        20        30        40
           .         .         .         .
CGCCCAGCGAAGAGCCGGGGTTCAACCTCACACTGGCCGA    40
CCTGGACTGGGATGCTTCCCCCGGCAACGACTCGCTGGGC    80
GACGAGCTGCTGCAGCTCTTCCCCGCGCCGCTGCTGGCGG   120
GCGTCACAGCCACCTGCGTGGCACTCTTCGTGGTGGGTAT   160
CGCTGGCAACCTGCTCACCATGCTGGTGGTGTCGCGCTTC   200

210       220       230       240
           .         .         .         .
CGCGAGCTGCGCACCACCACCAACCTCTACCTGTCCAGCA   240
TGGCCTTCTCCGATCTGCTCATCTTCCTCTGCATGCCCCT   280
GGACCTCGTTCGCCTCTGGCAGTACCGGCCCTGGAACTTC   320
GGCGACCTCCTCTGCAAACTCTTCCAATTCGTCAGTGAGA   360
GCTGCACCTACGCCACGGTGCTCACCATCACAGCGCTGAG   400

410       420       430       440
           .         .         .         .
CGTCGAGCGCTACTTCGCCATCTGCTTCCCACTCCGGGCC   440
AAGGTGGTGGTCACCAAGGGGCGGGTGAAGCTGGTCATCT   480
TCGTCATCTGGGCCGTGGCCTTCTGCAGCGCCGGGCCCAT   520
CTTCGTGCTAGTCGGGGTGGAGCACGAGAACGGCACCGAC   560
CCTTGGGACACCAACGAGTGCCGCCCCACCGAGTTTGCGG   600

610       620       630       640
           .         .         .         .
TGCGCTCTGGACTGCTCACGGTCATGGTGTGGGTGTCCAG   640
CATCTTCTTCTTCCTTCCTGTCTTCTGTCTCACGGTCCTC   680
TACAGTCTCATCGGCAGGAAGCTGTGGCGGAGGAGGCGCG   720
GCGATGCTGTCGTGGGTGCCTCGCTCAGGGACCAGAACCA   760
CAAGCAAACCGTGAAAATGCTGGCTGTAGTGGTGTTTGCC   800

810       820       830       840
           .         .         .         .
TTCATCCTCTGCTGGCTCCCCTTCCACGTAGGGCGATATT   840
TATTTTCCAAATCCTTTGAGCCTGGCTCCTTGGAGATTGC   880
TCAGATCAGCCAGTACTGCAACCTCGTGTCCTTTGTCCTC   920
TTCTACCTCAGTGCTGCCATCAACCCCATTCTGTACAACA   960
TCATGTCCAAGAAGTACCGGGTGGCAGTGTTCAGACTTCT  1000

1010      1020      1030      1040
           .         .         .         .
GGGATTCGAACCCTTCTCCCAGAGAAAGCTCTCCACTCTG  1040
AAAGATGAAAGTTCTCGGGCCTGGACAGAATCTAGTATTA  1080
ATACATGA    1088
```

FIG. 6

```
                10          20
                 .           .
        MLVVSRFREL  RTTTNLYLSS   20
        MAFSDLLIFL  CMPLDLVRLW   40
        QYRPWNFGDL  LCKLFQFVSE   60
        SCTYATVLTI  TALSVERYFA   80
        ICFPLRAKVV  VTKGRVKLVI  100

110         120
                 .           .
        FVIWAVAFCS  AGPIFVLVGV  120
        EHENGTDPWD  TNECRPTEFA  140
        VRSGLLTVMV  WVSSIFFFLP  160
        VFCLTVLYSL  IGRKLWRRRR  180
        GDAVVGASLR  DQNHKQTVKM  200

210         220
                 .           .
        LAVVVFAFIL  CWLPFHVGRY  220
        LFSKSFEPGS  LEIAQISQYC  240
        NLVSFVLFYL  SAAINPILYN  260
        IMSKKYRVAV  FRLLGFEPFS  280
        QRKLSTLKDE  SSRAWTESSI  300

```
1                                           30
PSEEPGFNLT  LADLDWDASP  GNDSLGDELL

HELIX 1      60
QLFPAP LLAG  VTATCVALFV  VGIAGNLLTM

HELIX 2          90
L VVSRFRELR  TTTNLYLSSM  AFSDLLIFL C

120
MPLDLVRLWQ   YRPWNFGDLL  CK LFQFVSES

HELIX 3                              150
CTYATVLTIT   ALSV ERY F AI  CFPLRAKVVV

HELIX 4         180
TKGRVK LVIF  VIWAVAFCSA  GPIFVLVG V E

210
HENGTDPWDT   NECRPTEFAV  R SGLLTVMVW

HELIX 5                       240
VSSIFFFLPV   FCLTVLYSLI  G RKLWRRRRG

HELIX 6  270
DAVVGASLRD   QNHKQT VKML  AVVVFAFILC

300
WLPFHVG RYL  FSKS FEPGSL  EIAQISQYCN

HELIX 7                      330
LVSFVLFYLS   AAINPILYNI  MS KKYRVAVF

360
RLLGFEPFSQ   RKLSTLKDES  SRAWTESSIN

```
              10        20        30        40
               .         .         .         .
         GCGCCTCACGCTCCCGCTTCGCGGCGCCTGGTCCCTGCGG    40
         TCCCCACTCGCTGCGACGCTTTGGGAAGTGCGAGATGGAA    80
         CTGGATCGAGAACGCAAATGCGAGGCAGGGCTGGTGACAG   120
         CATCCTCCCTACGCGTCTGCACCCGCTCCTCCCTCGCACC   160
         CTCCCGCGCCTAAGCGGACCTCCTCGGGAGCCAGCTCGGT   200

210       220       230       240
               .         .         .         .
         CCAGCCTCCCAGCGCAGTCACGTCCCAGAGCCTGTTCAGC   240
         TGAGCCGGCAGCATGTGGAACGCGACGCCCAGCGAAGAGC   280
         CGGGGTTCAACCTCACACTGGCCGACCTGGACTGGGATGC   320
         TTCCCCCGGCAACGACTCGCTGGGCGACGAGCTGCTGCAG   360
         CTCTTCCCCGCGCCGCTGCTGGCGGGCGTCACAGCCACCT   400

410       420       430       440
               .         .         .         .
         GCGTGGCACTCTTCGTGGTGGGTATCGCTGGCAACCTGCT   440
         CACCATGCTGGTGGTGTCGCGCTTCCGCGAGCTGCGCACC   480
         ACCACCAACCTCTACCTGTCCAGCATGGCCTTCTCCGATC   520
         TGCTCATCTTCCTCTGCATGCCCCTGGACCTCGTTCGCCT   560
         CTGGCAGTACCGGCCCTGGAACTTCGGCGACCTCCTCTGC   600

610       620       630       640
               .         .         .         .
         AAACTCTTCCAATTCGTCAGTGAGAGCTGCACCTACGCCA   640
         CGGTGCTCACCATCACAGCGCTGAGCGTCGAGCGCTACTT   680
         CGCCATCTGCTTCCCACTCCGGGCCAAGGTGGTGGTCACC   720
         AAGGGGCGGGTGAAGCTGGTCATCTTCGTCATCTGGGCCG   760
         TGGCCTTCTGCAGCGCCGGGCCCATCTTCGTGCTAGTCGG   800

810       820       830       840
               .         .         .         .
         GGTGGAGCACGAGAACGGCACCGACCCTTGGGACACCAAC   840
         GAGTGCCGCCCCACCGAGTTTGCGGTGCGCTCTGGACTGC   880
         TCACGGTCATGGTGTGGGTGTCCAGCATCTTCTTCTTCCT   920
         TCCTGTCTTCTGTCTCACGGTCCTCTACAGTCTCATCGGC   960
         AGGAAGCTGTGGCGGAGGAGGCGCGGCGATGCTGTCGTGG  1000
```

FIG.9A

```
          1010      1020      1030      1040
           .         .         .         .
GTGCCTCGCTCAGGGACCAGAACCACAAGCAAACCGTGAA   1040
AATGCTGGGTGGGTCTCAGCGCGCGCTCAGGCTTTCTCTC   1080
GCGGGTCCTATCCTCTCCCTGTGCCTTCTCCCTTCTCTCT   1120
GA  1122
```

FIG.9B

```
            10        20        30        40
             .         .         .         .
    MWNATPSEEPGFNLTLADLDWDASPGNDSLGDELLQLFPA   40
    PLLAGVTATCVALFVVGIAGNLLTMLVVSRFRELRTTTNL   80
    YLSSMAFSDLLIFLCMPLDLVRLWQYRPWNFGDLLCKLFQ  120
    FVSESCTYATVLTITALSVERYFAICFPLRAKVVVTKGRV  160
    KLVIFVIWAVAFCSAGPIFVLVGVEHENGTDPWDTNECRP  200

210       220       230       240
             .         .         .         .
    TEFAVRSGLLTVMVWVSSIFFFLPVFCLTVLYSLIGRKLW  240
    RRRRGDAVVGASLRDQNHKQTVKMLGGSQRALRLSLAGPI  280
    LSLCLLPSL  289
```

FIG.10

```
            10        20        30        40
             .         .         .         .
    MPLDLVRLWQYRPWNFGDLLCKLFQFVSESCTYATVLTIT   40
    ALSVERYFAICFPLRAKVVVTKGRVKLVIFVIWAVAFCSA   80
    GPIFVLVGVEHENGTDPWDTNECRPTEFAVRSGLLTVMVW  120
    VSSIFFFLPVFCLTVLYSLIGRKLWRRRRGDAVVGASLRD  160
    QNHKQTVKMLAVVVFAFILCWLPFHVGRYLFSKSFEPGSL  200

210       220       230       240
             .         .         .         .
    EIAQISQYCNLVSFVLFYLSAAINPILYNIMSKKYRVAVF  240
    RLLGFEPFSQRKLSTLKDESSRAWTESSINT  271
```

FIG.12

```
         10        20        30        40
          .         .         .         .
ATCTGCTCATCTTCCTCTGCATGCCCCTGGACCTCGTTCG    40
CCTCTGGCAGTACCGGCCCTGGAACTTCGGCGACCTCCTC    80
TGCAAACTCTTCCAATTCGTCAGTGAGAGCTGCACCTACG   120
CCACGGTGCTCACCATCACAGCGCTGAGCGTCGAGCGCTA   160
CTTCGCCATCTGCTTCCCACTCCGGGCCAAGGTGGTGGTC   200

210       220       230       240
          .         .         .         .
ACCAAGGGGCGGGTGAAGCTGGTCATCTTCGTCATCTGGG   240
CCGTGGCCTTCTGCAGCGCCGGGCCCATCTTCGTGCTAGT   280
CGGGGTGGAGCACGAGAACGGCACCGACCCTTGGGACACC   320
AACGAGTGCCGCCCCACCGAGTTTGCGGTGCGCTCTGGAC   360
TGCTCACGGTCATGGTGTGGGTGTCCAGCATCTTCTTCTT   400

410       420       430       440
          .         .         .         .
CCTTCCTGTCTTCTGTCTCACGGTCCTCTACAGTCTCATC   440
GGCAGGAAGCTGTGGCGGAGGAGGCGCGGCGATGCTGTCG   480
TGGGTGCCTCGCTCAGGGACCAGAACCACAAGCAAACCGT   520
GAAAATGCTGGCTGTAGTGGTGTTTGCCTTCATCCTCTGC   560
TGGCTCCCCTTCCACGTAGGGCGATATTTATTTTCCAAAT   600

610       620       630       640
          .         .         .         .
CCTTTGAGCCTGGCTCCTTGGAGATTGCTCAGATCAGCCA   640
GTACTGCAACCTCGTGTCCTTTGTCCTCTTCTACCTCAGT   680
GCTGCCATCAACCCCATTCTGTACAACATCATGTCCAAGA   720
AGTACCGGGTGGCAGTGTTCAGACTTCTGGGATTCGAACC   760
CTTCTCCCAGAGAAAGCTCTCCACTCTGAAAGATGAAAGT   800

810       820       830       840
          .         .         .         .
TCTCGGGCCTGGACAGAATCTAGTATTAATACATGA   836
```

FIG.11

```
                                              v10           v20
FIG.3-SWINE TYPE I  CLONE 7-3orf   LTLPDLGWDAPPENDSLVEE
                                   LTLPDLGWDAPPENDSLVEE
FIG.5-SWINE TYPE II CLONE 1375m    LTLPDLGWDAPPENDSLVEE
                                              ^20           ^30
                                              v30           v40
FIG.3-SWINE TYPE I  CLONE 7-3orf   LLPLFPTPLLAGVTATCVAL
                                   LLPLFPTPLLAGVTATCVAL
FIG.5-SWINE TYPE II CLONE 1375m    LLPLFPTPLLAGVTATCVAL
                                              ^40           ^50
                                              v50           v60
FIG.3-SWINE TYPE I  CLONE 7-3orf   FVVGIAGNLLTMLVVSRFRE
                                   FVVGIAGNLLTMLVVSRFRE
FIG.5-SWINE TYPE II CLONE 1375m    FVVGIAGNLLTMLVVSRFRE
                                              ^60           ^70
                                              v70           v80
FIG.3-SWINE TYPE I  CLONE 7-3orf   MRTTTNLYLSSMAFSDLLIF
                                   MRTTTNLYLSSMAFSDLLIF
FIG.5-SWINE TYPE II CLONE 1375m    MRTTTNLYLSSMAFSDLLIF
                                              ^80           ^90
                                              v90          v100
FIG.3-SWINE TYPE I  CLONE 7-3orf   LCMPLDLFRLWQYRPWNLGN
                                   LCMPLDLFRLWQYRPWNLGN
FIG.5-SWINE TYPE II CLONE 1375m    LCMPLDLFRLWQYRPWNLGN
                                              ^100          ^110
                                              v110         v120
FIG.3-SWINE TYPE I  CLONE 7-3orf   LLCKLFQFVSESCTYATVLT
                                   LLCKLFQFVSESCTYATVLT
FIG.5-SWINE TYPE II CLONE 1375m    LLCKLFQFVSESCTYATVLT
                                              ^120          ^130
                                              v130         v140
FIG.3-SWINE TYPE I  CLONE 7-3orf   ITALSVERYFAICFPLRAKV
                                   ITALSVERYFAICFPLRAKV
FIG.5-SWINE TYPE II CLONE 1375m    ITALSVERYFAICFPLRAKV
                                              ^140          ^150
                                              v150         v160
FIG.3-SWINE TYPE I  CLONE 7-3orf   VVTKGRVKLVILVIWAVAFC
                                   VVTKGRVKLVILVIWAVAFC
FIG.5-SWINE TYPE II CLONE 1375m    VVTKGRVKLVILVIWAVAFC
                                              ^160          ^170
```

FIG.13A

```
                                                        v170         v180
FIG.3-SWINE TYPE I CLONE 7-3orf    SAGPIFVLVGVEHDNGTDPR
                                   SAGPIFVLVGVEHDNGTDPR
FIG.5-SWINE TYPE II CLONE 1375m    SAGPIFVLVGVEHDNGTDPR
                                          ^180         ^190
                                                        v190         v200
FIG.3-SWINE TYPE I CLONE 7-3orf    DTNECRATEFAVRSGLLTVM
                                   DTNECRATEFAVRSGLLTVM
FIG.5-SWINE TYPE II CLONE 1375m    DTNECRATEFAVRSGLLTVM
                                          ^200         ^210
                                                        v210         v220
FIG.3-SWINE TYPE I CLONE 7-3orf    VWVSSVFFFLPVFCLTVLYS
                                   VWVSSVFFFLPVFCLTVLYS
FIG.5-SWINE TYPE II CLONE 1375m    VWVSSVFFFLPVFCLTVLYS
                                          ^220         ^230
                                                        v230         v240
FIG.3-SWINE TYPE I CLONE 7-3orf    LIGRKLWRRKRGEAAVGSSL
                                   LIGRKLWRRKRGEAAVGSSL
FIG.5-SWINE TYPE II CLONE 1375m    LIGRKLWRRKRGEAAVGSSL
                                          ^240         ^250
                                                        v250         v260
FIG.3-SWINE TYPE I CLONE 7-3orf    RDQNHKQTVKMLAVVVFAFI
                                   RDQNHKQTVKML:     A:
FIG.5-SWINE TYPE II CLONE 1375m    RDQNHKQTVKMLGGSQCALE
                                          ^260         ^270
                                                        v270
FIG.3-SWINE TYPE I CLONE 7-3orf    LCWL-PFHVGRYLFSKS
                                   L.   P:H :..LFS.:
FIG.5-SWINE TYPE II CLONE 1375m    LSLPGPLH-SSCLFSSP
                                          ^280
```

FIG. 13B

```
                                                  v10         v20
FIG.8-HUMAN TYPE I 1146orf          PSEEPGFNLTLADLDWDASP
                                    PSEEPGFNLTLADLDWDASP
FIG.10-HUMAN TYPE II CLONE1141m     PSEEPGFNLTLADLDWDASP
                                        ^10         ^20
                                                  v30         v40
FIG.8-HUMAN TYPE I 1146orf          GNDSLGDELLQLFPAPLLAG
                                    GNDSLGDELLQLFPAPLLAG
FIG.10-HUMAN TYPE II CLONE1141m     GNDSLGDELLQLFPAPLLAG
                                        ^30         ^40
                                                  v50         v60
FIG.8-HUMAN TYPE I 1146orf          VTATCVALFVVGIAGNLLTM
                                    VTATCVALFVVGIAGNLLTM
FIG.10-HUMAN TYPE II CLONE1141m     VTATCVALFVVGIAGNLLTM
                                        ^50         ^60
                                                  v70         v80
FIG.8-HUMAN TYPE I 1146orf          LVVSRFRELRTTTNLYLSSM
                                    LVVSRFRELRTTTNLYLSSM
FIG.10-HUMAN TYPE II CLONE1141m     LVVSRFRELRTTTNLYLSSM
                                        ^70         ^80
                                                  v90        v100
FIG.8-HUMAN TYPE I 1146orf          AFSDLLIFLCMPLDLVRLWQ
                                    AFSDLLIFLCMPLDLVRLWQ
FIG.10-HUMAN TYPE II CLONE1141m     AFSDLLIFLCMPLDLVRLWQ
                                        ^90        ^100
                                                 v110        v120
FIG.8-HUMAN TYPE I 1146orf          YRPWNFGDLLCKLFQFVSES
                                    YRPWNFGDLLCKLFQFVSES
FIG.10-HUMAN TYPE II CLONE1141m     YRPWNFGDLLCKLFQFVSES
                                        ^100        ^110
                                                 v130        v140
FIG.8-HUMAN TYPE I 1146orf          CTYATVLTITALSVERYFAI
                                    CTYATVLTITALSVERYFAI
FIG.10-HUMAN TYPE II CLONE1141m     CTYATVLTITALSVERYFAI
                                        ^130        ^140 v150        v160
FIG.8-HUMAN TYPE I 1146orf          CFPLRAKVVVTKGRVKLVIF
                                    CFPLRAKVVVTKGRVKLVIF
FIG.10-HUMAN TYPE II CLONE1141m     CFPLRAKVVVTKGRVKLVIF
                                        ^150        ^160
```

FIG.14A

```
                                              v170        v180
FIG.8-HUMAN TYPE I 1146orf           VIWAVAFCSAGPIFVLVGVE
                                     VIWAVAFCSAGPIFVLVGVE
FIG.10-HUMAN TYPE II CLONE1141m      VIWAVAFCSAGPIFVLVGVE
                                              ^170        ^180
                                              v190        v200
FIG.8-HUMAN TYPE I 1146orf           HENGTDPWDTNECRPTEFAV
                                     HENGTDPWDTNECRPTEFAV
FIG.10-HUMAN TYPE II CLONE1141m      HENGTDPWDTNECRPTEFAV
                                              ^190        ^200
                                              v210        v220
FIG.8-HUMAN TYPE I 1146orf           RSGLLTVMVWVSSIFFFLPV
                                     RSGLLTVMVWVSSIFFFLPV
FIG.10-HUMAN TYPE II CLONE1141m      RSGLLTVMVWVSSIFFFLPV
                                              ^210        ^220
                                              v230        v240
FIG.8-HUMAN TYPE I 1146orf           FCLTVLYSLIGRKLWRRRRG
                                     FCLTVLYSLIGRKLWRRRRG
FIG.10-HUMAN TYPE II CLONE1141m      FCLTVLYSLIGRKLWRRRRG
                                              ^230        ^240
                                              v250        v260
FIG.8-HUMAN TYPE I 1146orf           DAVVGASLRDQNHKQTVKML
                                     DAVVGASLRDQNHKQTVKML
FIG.10-HUMAN TYPE II CLONE1141m      DAVVGASLRDQNHKQTVKML
                                              ^250        ^260
```

FIG.14B

```
                                                v10        v20        v30        v40
FIG.3-SWINE TYPE I CLONE 7-3orf   LTLPDLGWDAPPENDSLVEELLPLFPTPLLAGVTATCVAL
                                  LTL:DL:WDA:P.NDSL :ELL.LFP:PLLAGVTATCVAL
FIG.8-HUMAN TYPE I 1146orf        LTLADLDWDASPGNDSLGDELLQLFPAPLLAGVTATCVAL
                                    ^10        ^20        ^30        ^40
                                                v50        v60        v70        v80
FIG.3-SWINE TYPE I CLONE 7-3orf   FVVGIAGNLLTMLVVSRFREMRTTTNLYLSSMAFSDLLIF
                                  FVVGIAGNLLTMLVVSRFRE:RTTTNLYLSSMAFSDLLIF
FIG.8-HUMAN TYPE I 1146orf        FVVGIAGNLLTMLVVSRFRELRTTTNLYLSSMAFSDLLIF
                                    ^50        ^60        ^70        ^80
                                                v90       v100       v110       v120
FIG.3-SWINE TYPE I CLONE 7-3orf   LCMPLDLFRLWQYRPWNLGNLLCKLFQFVSESCTYATVLT
                                  LCMPLDL RLWQYRPWN:G:LLCKLFQFVSESCTYATVLT
FIG.8-HUMAN TYPE I 1146orf        LCMPLDLVRLWQYRPWNFGDLLCKLFQFVSESCTYATVLT
                                    ^90       ^100       ^110       ^120
                                               v130       v140       v150       v160
FIG.3-SWINE TYPE I CLONE 7-3orf   ITALSVERYFAICFPLRAKVVVTKGRVKLVILVIWAVAFC
                                  ITALSVERYFAICFPLRAKVVVTKGRVKLVI:VIWAVAFC
FIG.8-HUMAN TYPE I 1146orf        ITALSVERYFAICFPLRAKVVVTKGRVKLVIFVIWAVAFC
                                   ^130       ^140       ^150       ^160
                                               v170       v180       v190       v200
FIG.3-SWINE TYPE I CLONE 7-3orf   SAGPIFVLVGVEHDNGTDPRDTNECRATEFAVRSGLLTVM
                                  SAGPIFVLVGVEH:NGTDP:DTNECR:TEFAVRSGLLTVM
FIG.8-HUMAN TYPE I 1146orf        SAGPIFVLVGVEHENGTDPWDTNECRPTEFAVRSGLLTVM
                                   ^170       ^180       ^190       ^200
                                               v210       v220       v230       v240
FIG.3-SWINE TYPE I CLONE 7-3orf   VWVSSVFFFLPVFCLTVLYSLIGRKLWRRKRGEAAVGSSL
                                  VWVSS:FFFLPVFVLTVLYSLIGRKLWRR:RG:A.VG:SL
FIG.8-HUMAN TYPE I 1146orf        VWVSSIFFFLPVFCLTVLYSLIGRKLWRRRRGDAVVGASL
                                   ^210       ^220       ^230       ^240
                                               v250       v260       v270       v280
FIG.3-SWINE TYPE I CLONE 7-3orf   RDQNHKQTVKMLAVVVFAFILCWLPFHVGRYLFSKSLEPG
                                  RDQNHKQTVKMLAVVVFAFILCWLPFHVGRYLFSKS:EPG
FIG.8-HUMAN TYPE I 1146orf        RDQNHKQTVKMLAVVVFAFILCWLPFHVGRYLFSKSFEPG
                                   ^250       ^260       ^270       ^280
                                               v290       v300       v310       v320
FIG.3-SWINE TYPE I CLONE 7-3orf   SVEIAQISQYCNLVSFVLFYLSAAINPILYNIMSKKYRVA
                                  S:EIAQISQYCNLVSFVLFYLSAAINPILYNIMSKKYRVA
FIG.8-HUMAN TYPE I 1146orf        SLEIAQISQYCNLVSFVLFYLSAAINPILYNIMSKKYRVA
                                   ^290       ^300       ^310       ^320
                                               v330       v340       v350
FIG.3-SWINE TYPE I CLONE 7-3orf   VFKLLGFEPFSQRKLSTLKDESSRAWTESSINT
                                  VF:LLGFEPFSQRKLSTLKDESSRAWTESSINT
FIG.8-HUMAN TYPE I 1146orf        VFRLLGFEPFSQRKLSTLKDESSRAWTESSINT
                                   ^330       ^340       ^350       ^360
```

FIG.15

| | v10 v20 |
|---|---|
| FIG.5-SWINE TYPE II CLONE 1375m | MWNATPSEEPGPNLTLPDLG |
| | MWNATPSEEPG NLTL:DL: |
| FIG.10-HUMAN TYPE II CLONE1141m | MWNATPSEEPGFNLTLADLD |
| | ^10 ^20 |
| | v30 v40 |
| FIG.5-SWINE TYPE II CLONE 1375m | WDAPPENDSLVEELLPLFPT |
| | WDA:P.NDSL :ELL.LFP: |
| FIG.10-HUMAN TYPE II CLONE1141m | WDASPGNDSLGDELLQLFPA |
| | ^30 ^40 |
| | v50 v60 |
| FIG.5-SWINE TYPE II CLONE 1375m | PLLAGVTATCVALFVVGIAG |
| | PLLAGVTATCVALFVVGIAG |
| FIG.10-HUMAN TYPE II CLONE1141m | PLLAGVTATCVALFVVGIAG |
| | ^50 ^60 |
| | v70 v80 |
| FIG.5-SWINE TYPE II CLONE 1375m | NLLTMLVVSRFREMRTTTNL |
| | NLLTMLVVSRFRE:RTTTNL |
| FIG.10-HUMAN TYPE II CLONE1141m | NLLTMLVVSRFRELRTTTNL |
| | ^70 ^80 |
| | v90 v100 |
| FIG.5-SWINE TYPE II CLONE 1375m | YLSSMAFSDLLIFLCMPLDL |
| | YLSSMAFSDLLIFLCMPLDL |
| FIG.10-HUMAN TYPE II CLONE1141m | YLSSMAFSDLLIFLCMPLDL |
| | ^90 ^100 |
| | v110 v120 |
| FIG.5-SWINE TYPE II CLONE 1375m | FRLWQYRPWNLGNLLCKLFQ |
| | RLWQYRPWN:G:LLCKLFQ |
| FIG.10-HUMAN TYPE II CLONE1141m | VRLWQYRPWNFGDLLCKLFQ |
| | ^110 ^120 |
| | v130 v140 |
| FIG.5-SWINE TYPE II CLONE 1375m | FVSESCTYATVLTITALSVE |
| | FVSESCTYATVLTITALSVE |
| FIG.10-HUMAN TYPE II CLONE1141m | FVSESCTYATVLTITALSVE |
| | ^130 ^140 |
| | v150 v160 |
| FIG.5-SWINE TYPE II CLONE 1375m | RYFAICFPLRAKVVVTKGRV |
| | RYFAICFPLRAKVVVTKGRV |
| FIG.10-HUMAN TYPE II CLONE1141m | RYFAICFPLRAKVVVTKGRV |
| | ^150 ^160 |

FIG.16A

|  |  |
|---|---|
| | v170     v180 |
| FIG.5-SWINE TYPE II CLONE 1375m | KLVILVIWAVAFCSAGPIFV |
| | KLVI:VIWAVAFCSAGPIFV |
| FIG.10-HUMAN TYPE II CLONE1141m | KLVIFVIWAVAFCSAGPIFV |
| | ^170     ^180 |
| | v190     v200 |
| FIG.5-SWINE TYPE II CLONE 1375m | LVGVEHDNGTDPRDTNECRA |
| | LVGVEH:NGTDP:DTNECR: |
| FIG.10-HUMAN TYPE II CLONE1141m | LVGVEHENGTDPWDTNECRP |
| | ^190     ^200 |
| | v210     v220 |
| FIG.5-SWINE TYPE II CLONE 1375m | TEFAVRSGLLTVMVWVSSVF |
| | TEFAVRSGLLTVMVWVSS:F |
| FIG.10-HUMAN TYPE II CLONE1141m | TEFAVRSGLLTVMVWVSSIF |
| | ^210     ^220 |
| | v230     v240 |
| FIG.5-SWINE TYPE II CLONE 1375m | FFLPVFCLTVLYSLIGRKLW |
| | FFLPVFCLTVLYSLIGRKLW |
| FIG.10-HUMAN TYPE II CLONE1141m | FFLPVFCLTVLYSLIGRKLW |
| | ^230     ^240 |
| | v250     v260 |
| FIG.5-SWINE TYPE II CLONE 1375m | RRKRGEAAVGSSLRDQNHKQ |
| | RR:RG:A.VG:SLRDQNHKQ |
| FIG.10-HUMAN TYPE II CLONE1141m | RRRRGDAVVGASLRDQNHKQ |
| | ^250     ^260 |
| | v270     v280 |
| FIG.5-SWINE TYPE II CLONE 1375m | TVKMLGGSQCALELSLPGPL |
| | TVKMLGGSQ AL LSL:GP: |
| FIG.10-HUMAN TYPE II CLONE1141m | TVKMLGGSQRALRLSLAGPI |
| | ^270     ^280 |
| FIG.5-SWINE TYPE II CLONE 1375m | HSSCLFSS |
| | S CL::S |
| FIG.10-HUMAN TYPE II CLONE1141m | LSLCLLPS |

FIG.16B

| (100Nm) | SWINE CLONE 7-3 | | HUMAN CLONE 1146 | |
|---|---|---|---|---|
| | 24 HOURS | 48 HOURS | 24 HOURS | 48 HOURS |
| COMPOUND A (100nm) | 13,553 | 2,692 | 1,353 | 2,228 |
| (1000 nM) | 9,176 | | 3,091 | |
| COMPOUND B (100nM) | 717 | 425 | 113 | 108 |
| COMPOUND C (100nM) | 100 | 58 | 96 | 67 |
| GHRP-2 (1000 nM) | 2,492 | | 1542 | |
| GHRP-6 (1000 nM) | 5,003 | | 617 | |

| LIGAND | INHIBITION (% OF CONTROL SPECIFIC BINDING) |
|---|---|
| COMPOUND A @ 5nM | 97 |
| GHRP-6 @ 10nM | 84 |
| COMPOUND C | |
| 1.692,428 @ 1 μM | 43 |
| GALAMIN @ 10 μM | 44 |
| AMENOMEDIN N @ 10 μM | 19 |

```
  1  MWNATPSEEP GFNLTLADLD WDASPGNDSL GDELLQLFPA PLLAGVTATC

51  VALFVVGIAG NLLTMLVVSR FRELRTTTNL YLSSMAFSDL LIFLCMPLDL

101  VRLWQYRPWN FGDLLCKLFQ FVSESCTYAT VLTITALSVE RYFAICFPLR

151  AKVVVTKGRV KLVIFVIWAV AFCSAGPIFV LVGVEHENGT DPWDTNECRP

201  TEFAVRSGLL TVMVWVSSIF FFLPVFCLTV LYSLIGRKLW RRRRGDAVVG

251  ASLRDQNHKQ TVKMLAVVVF AFILCWLPFH VGRYLFSKSF EPGSLEIAQI

301  SQYCNLVSFV LFYLSAAINP ILYNIMSKKY RVAVFRLLGF EPFSQRKLST

351  LKDESSRAWT ESSINT*
```

FIG.22

```
          .         .         .         .         .         .
         10        20        30        40        50        60
ATG TGG AAC GCG ACC CCC AGC GAG GAG CCT AAC GTC ACG TTG GAC CTG GAT TGG CCG       60
GAC GCT TCC CCC GGC GTC ACC GCC GAC TCA CTG CCT GAA CTG CTG CCG CTG TTC CCC AAC  120
CTG CTG GCA GGC GTC CTG GCC ACC TGC GCG CCG GAG GCG CTC GTG GTG GGC ATC TCA GGC CTC  180
CTG CTC ACT ATG GCC GTG GTG TCC CGC GTG TTC CGC GAG CTG CTG CGC CTG ACC AAC CTC TAC  240
CTG TCC AGC ATG GCC TTC TCG GAT CTG CTC ATC TTC CTG TGC ATG CCG CTG GAC CTC GTC  300
          .         .         .         .         .         .
         310       320       330       340       350       360
CGC CTC TGG CAG TAC CGG CCC TGG AAC TTC GGC GAC CTG CTC AAA CTC TTC CAG TTT  360
GTC AGC GAG AGC TGC ACC TAC TGC CTG CTG GCC GTC ACG GTC CTG AGC CTG GAG CGC  420
TAC TTC GCC ATC TGC TTC CCT CTG CGG GCC AAG GTG GTC ACT AAG GGC CGC GTG AAG CGC  480
CTG GTC ATC CTT GTC ATC TGG GCC GTG GCT TTC TGC AGC GCG CCC ATC TTC GTG CTG  540
GTG GGC GTG GAG CAC GAA AAC GGC ACA GAT CCC CGG GAC ACC GAA TGC CGC GCC ACC  600
          .         .         .         .         .         .
         610       620       630       640       650       660
GAG TTC GCT GTG CGC TCT GGG CTG CTC ACC GTC ATG GTG TGG GTG TCC AGC GTC TTC  660
TTT CTA CCG GTC TTC TGC TTC CTC ACT GTG CTC TAC AGT CTC ATC GGG AGG AAG CTA TCG CGG  720
AGA CGC GGA GAT GCA GCG GTG GCC TCG GGC GTC CTC GGC GAC CAG AAC CAC AAG CAG ACA GTG  780
AAG ATG CTT Ggt gag tcc tgg cac ccg ctg acc ctt ccc cca gtc cct gcc ctt ccc  840
cag cgg cct cta ttt ctg ttt ctc atc atc tcc gct ccc caa gtc tct caa gtc tct gtc  900
```

FIG.27A

```
         910       920       930       940       950       960
          .         .         .         .         .         .
ttt ctc tgc ctc tct cac ctt ggt tct cgg tct cac tgc ttt tct tcc tgt ctt    960
ttc ctg tat ctt gtc cac gaa gaa gat cca tca tat tgg taa ttc ctt aaa acg agg aac   1020
ctt ggt ctg gga aaa ttg gtc caa gat gga aat acc tca cgg ttt att gag ccc cta att   1080
gtt aac ggt tta gct tct tgt ctc aca tag aat ttg tgg tta tca aag taa taa tat taa   1140
ggt aag cag gca ggt aat ggg ttt aga aat cac tcc atg gta agt cta acc aca aat ttg   1200

1210      1220      1230      1240      1250      1260
          .         .         .         .         .         .
ggt cac tct gtt aag gac ggc tta tag atg tat ttt gtt tgt ttt caa tat tgg gat ttg   1260
ttt tct gcc ctg cat ctt tct cag ata att aca tcc act ctg ttt agt cta tgg ttt tgc   1320
cag gag ggg ctt cat gct ggg gtc tcc ttc ttt ttg tat ttg tct ccc cag taa           1380
tat agg cca gga tag ggt gga gaa gtc atc ctt tcc tca aac tgt cct tca gga agg tct   1440
ggg tac tga acg gtt act gca taa act ctg ctt ccc caa agg cat gtg ctt ggt gtg gta   1500

1510      1520      1530      1540      1550      1560
          .         .         .         .         .         .
aag tca aga tgg tgc tca tgt cca aga gga acc tct gat ctc act ttt caa ggg att      1560
tca tgt ttg ctg aca ttt aat act tgt tag ttt ttg cag ggg gat gat ttc tca ttt gca   1620
att tta tta ttc tca aat tct gca tgt cag aat gtt aga gat ttc tca ggg atg tca ggt   1680
tct gtt tcc aga tga gtg att gcc ctg tgt cct ctg tgt aaa ctc ata tgc acc           1740
aga cag ggt cta tga acg tgc cgt tgc cat tgc tcc atg cct tcc atg tgt cac tta gtc cta aag   1800
```

FIG.27B

```
       1810        1820        1830        1840        1850        1860
         .           .           .           .           .           .
aga agt tac taa cct aat ctc act aat ctc act ggc atc tca atg ccg atc cca ttg  1860
tca tct gaa aat ttg aag ggg aca tta aag tgg cac agg gac cag aac aat att ttt ctc  1920
tca ttg ctg aat ttt aaa aac cta aaa aat tgg aat tct tga aga aac tct ctt ata  1980
tga cta aaa tga agc ctt ggg tgg agc ttt att att gtc tgg ctt acc tgc ccc ccc  2040
cac tac tta tat ctt tta gag atg aca cag act tgc ttt ccc tgt ggc tac taa tcc caa  2100

2110        2120        2130        2140        2150        2160
         .           .           .           .           .           .
ttg cac att cag tcc ctt gat aga ctt act cta aaa atc taa gtt cag cgg tcc acg aaa  2160
cat aac aaa gcc tgt cct aaa aca aga aag aaa gaa aga aag gca aga aag aaa  2220
gca aga aag aga aga gaa aga aga aac cag aag gtc ttt ccc cat tcc cta aca tac  2280
agg aat gga aat tat taa gtc tac gtg ata gcc aat gca tct gtt tct gtt tca gta tgc cca  2340
caa ggg tgc tgc cgg agc cat tgc tca ggg ctg gag tat tta ctg ggc atg ctt gac ccc  2400

2410        2420        2430        2440        2450        2460
         .           .           .           .           .           .
agc atg gag ggt gag aag tgc tcc tgg gaa ctc tga tcc act gct gtg gag agc aaa  2460
cac ctg gcc tca ttt ata ctt gtt ctt gtc cat gtc agt cat ata atg cat ata aat ggg gga taa tca tta  2520
cta aac tgt tta gct gag cct cat gtc agt gtc caa tca caa agc aga gta att acc aca cag  2580
act ggg aag ctc agt gaa gat gat tgt tag cgg ttg gtc tga cag tct tgc tgt gtg cta tag  2640
tgt tag acc caa cgg agg cag tat tta toa gga ggg cag ggt tcc atg ttt ccc gtg tta  2700
```

FIG.27C

```
        2710       2720       2730       2740       2750       2760
aag agc aag aga tga tgt ttg tca gta ggc atg cag ctc atg gtg aaa aga aag tcc aga  2760
ctt aaa gat gtg gtg aag ttt gtg ttt gct ctt tgc ccc acc ctg aca gtc tct ctc tgt gtg cst  2820
tca GCT GTG GTG GTG TTT GCT CTC ATC CTC TGC CTG CCC TTC CAC GTG GGA AGA TAC  2880
CTC TTT TCC AAG TCC TTC GAG CCT GGC TCT CTG GAG ATC GCT AGC CAG ATC TAC TGC  2940
AAC CTG GTG TCC TTT GTC CTC TAC CTC TTC AGC GCT GCC ATC AAC CCC ATT CTG TAC AAC  3000
        3010       3020       3030       3040       3050       3060
ATC ATG TCC AAG AAG TAC CGG GTG GCA GTG TTC AAA CTG CTA GGA TTT GAA TCC TTC TCC  3060
CAG AGA AAG CTT TCC ACT CTG AAG GAT GAG AGT TCC CGG GCC TGG ACA AAG TCG AGC ATC  3120
AAC ACA TGA  3129
```

FIG. 27D

```
          10          20          30          40          50          60
ATG TGG AAC GCG ACC CCC AGC GAG GAG CCT AAC GTC CTG GAC TTG GAT TGG     60
GAC GCT TCC CCC GGC AAC GAC TCA CTG CCT GAA CTG CCG TTC CCC GCT CCG    120
CTG CTG GCA GGC GTC ACC GCC GTG TGC ACC GCG CTC TTC GTG GGC ATC ACC AAC    180
CTC CTC ACT ATG CTG GTG GTG CTG CGC TTC CCC CGC GAG CTG CGC ACC AAC CTC TAC    240
CTG TCC AGC ATG GCC TTC TCG GAT CTG CTC ATC TTC TGC ATG CCG CTG GAC CTC GTC    300

310         320         330         340         350         360
CGC CTC TGG CAG TAC CGG CCC TGG AAC TTC GGC GAC CTG CTC AAA CTC TTC CAG TTT    360
GTC ACC GAG AGC TGC TTC ACC ACG CTG GCC CTC ACC ATC ACC GCG CTG AGC GTC GAG CGC    420
TAC TTC GCC ATC TGC TTC CCT CTG CGG GCC AAG GTG GTC ACT AAG GGC CGC TTC GTG AAG    480
CTG GTC ATC CTT GTC ATC TGG GCC GCT GGC TTC CCC AGC GCG ACC GAA TGC CGC GCC CTG    540
GTG GGC GTG GAG CAC GAA AAC GGC ACA GAT CCC CGG GAC AAC AAC GGG CCC ATC TGC GCC ACC    600

610         620         630         640         650         660
GAG TTC GCT GTG CGC TCT CTG GGG CTG CTC ACC GTC ATG GTG TGG TCC AGC GTC TTC TTC    660
TTT CTA CCG GTC TTC TGC GCA GCG GTG GTG CTC ACT GTG CTC TAC AGT CTC ATC GGG AAC AAG AAG CAC CTA TGG CGG    720
AGA CGC GGA GAT GCA GTT GCT GTG GTG GGC GTG TTT GCT GTC TGC TGG TTG CCC GAG AAC ATC AGC AGC GTG GGA    780
AAG ATG CTT GCT GTG GTG GTG TCC TGC TTC TCT GAG CCT CTG GAG ATC TTC CAC ATC AGC    840
AGA TAC CTC CTC TTT CCC AAG TCC TTC TTC GGC CTC TCT CTG CTG CAG ATC AGC CAG CAG    900
```

FIG. 28A

```
      910         920         930         940         950         960
TAC TGC AAC CTG GTG TCC TTT GTC CTC TTC TAC CTC AGC GCT GCC ATC AAC CCC ATT CTG
TAC AAC ATC ATG TCC AAG AAG TAC CGG GTG GCA GTG TTC AAA CTG CTA GGA TTT GAA TCC 1020
TTC TCC CAG AGA AAG CTT TCC ACT CTG AAG GAT GAG AGT TCC CGG GCC TGG ACA AAG TCG 1080
AGC ATC AAC ACA  1092
```

FIG.28B

```
           10         20         30         40         50
            .          .          .          .          .
MWNATPSEEP EPNVTLDLDW DASPGNDSLP DELLPLFPAP LLAGVTATCV    50
ALFVVGISGN LLTNLVVSRF RELRTTTNLY LSSMAFSDLL IFLCMPLDLV   100
RLWQYRPWNF GDLLCKLFQF VSESCTYATV LTITALSVER YFAICFPLRA   150
KVVVTKGRVK LVILVIWAVA FCSAGPIFVL VGVEHENGTD PRDTNECRAT   200
EFAVRSGLLT VMVWVSSVFF FLPVFCLTVL YSLIGRKLWR RRGDAAVGAS   250

260        270        280        290        300
            .          .          .          .          .
LRDQNHKQTV KMLAVVVFAF ILCWLPFHVG RYLFSKSFEP GSLEIAQISQ   300
YCNLVSFVLF YLSAAINPIL YNIMSKKYRV AVFKLLGFES FSQRKLSTLK   350
DESSRAWTKS SINT   364
```

FIG.29

ASSAYS FOR GROWTH HORMONE SECRETAGOGUE RECEPTORS

CROSS-REFERENCE TO RELATED APPLICATIONS

This application claims priority to U.S. provisional application Ser. No. 60/008,584 filed, Dec. 13, 1995 and U.S. provisional application Ser. No. 60/019,259, filed Jun. 6, 1996.

FIELD OF THE INVENTION

This invention relates to an assay which involves identification of cell membrane receptors, specifically growth hormone secretagogoue receptors (GHSRs). By varying the protocol, receptor ligands can be identified, or the presence of a GHSR can be identified.

BACKGROUND OF THE INVENTION

Growth hormone (GH) is an anabolic hormone capable of promoting linear growth, weight gain and whole body nitrogen retention. Classically, GH is thought to be released primarily from the somatotroph cells of the anterior pituitary under the coordinate regulation of two hypothalamic hormones, growth hormone releasing factor (GHRF or GRF) and somatostatin. Both GHRF stimulation and somatostatin inhibition of the release of GH occurs by the specific engagement of receptors on the cell membrane of the somatotroph.

Recent evidence has been mounting which suggests that GH release is also stimulated by a group of short peptides termed the growth hormone releasing peptides (GHRP; GHRP-6, GHRP-2 [hexarelin]) These peptides are described, for example, in U.S. Pat. No. 4,411,890, PCT Patent Pub. No. WO 89/07110, PCT Patent Pub. No. WO 89/07111, PCT Patent Pub. No. WO 93/04081, and J. Endocrinol Invest., 15(Suppl 4), 45 (1992). These peptides function by selectively binding to a distinct somatotroph cell membrane receptor, the growth hormone secretagogue receptor (GHSR). A medicinal chemical approach has resulted in the design of several classes of orally-active, low molecular weight, non-peptidyl compounds which bind specifically to this receptor and result in the pulsatile release of GH. Such compounds possessing growth hormone secretagogue activity are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; Science, 260, 1640–1643 (Jun. 11, 1993); Ann. Rep. Med. Chem., 28, 177–186 (1993); Bioorg. Med. Chem. Ltrs., 4(22), 2709–2714 (1994); and Proc. Natl. Acad. Sci. USA 92, 7001–7005 (July 1995).

The use of such orally-active agents which stimulate the pulsatile release of GH would be a significant advance in the treatment of growth hormone deficiency in children and adults as well as provide substantial benefit under circumstances where the anabolic effects of GH might be exploited clinically (e.g. post-hip fracture rehabilitation, the frail elderly and in post-operative recovery patients).

Cell membrane receptors which are of low abundance on the cells can be difficult to isolate, clone and characterize. In the past, assays to identify a receptor in a mammalian cell or frog oocyte generally have depended on either: 1) directly detecting a receptor-ligand interaction, such as by binding of a radiolabeled ligand; or 2) indirectly detecting receptor-ligand binding by detecting either an intracellular event (such as calcium mobilization, or the identification of, for instance a calcium activated current) or an extracellular event (such as hormone secretion), that is the consequence of the ligand binding to its receptor. Most cloned receptors, which have been isolated using a functional expression assay have relied on immortalized cell lines or tumor derived tissues which are enriched for the receptor of interest.

There are numerous receptors which cannot be readily identified using these types of assays, due to: 1) a paucity of biochemical information about the protein; 2) the low abundance of receptors present on the cell; and/or 3) the lack of a cell line or tumor material expressing the receptor. It would be desirable to develop an assay which can be used to identify and characterize cell receptors not amenable to study by conventional means.

DETAILED DESCRIPTION OF THE INVENTION

This invention relates to an assay method to determine the presence of a nucleic acid which encodes a G protein-linked cell membrane receptor comprising:
a) introducing at least one nucleic acid suspected of encoding a G protein cell membrane receptor into a cell;
b) introducing a G-protein subunit into the cell;
c) introducing a detector molecule or a nucleic acid encoding a detector molecule into the cell, wherein the detector molecule responds directly or indirectly to a G-protein receptor-ligand binding event;
d) contacting the cell with a receptor ligand; and
e) determining whether the oligonucleotide encoded a receptor by monitoring the detector molecule.

In one preferred embodiment the cell does not naturally express the receptor on its cell membrane. In other preferred embodiments of the assay, the receptor is a member of the growth hormone secretagogue family of receptors, such as a growth hormone secretagogue receptor (GHSR) or a growth hormone secretagogue related receptor (GHSRR). Thus, another aspect of this invention is an assay method to determine the presence of a nucleic acid which encodes a member of the growth hormone secretagogue receptor family comprising:
a) introducing at least one nucleic acid suspected of encoding a GHSR or GHSRR into a cell which does not naturally express the receptor on its cell membrane;
b) introducing a G-protein subunit into the cell;
c) introducing a detector molecule or a nucleic acid encoding a detector molecule into the cell, wherein the detector molecule is directly or indirectly responsive to a GHSR-ligand or GHSRR-ligand binding event;

d) contacting the cell with a growth hormone secretagogue; and e) determining whether the nucleic acid encodes a receptor by monitoring the detector molecule.

A further embodiment of this invention is an assay to determine the presence of a growth hormone secretagogue. Thus, this invention also comprises a method to determine the presence of a growth hormone secretagogue comprising:

a) introducing a nucleic acid which encodes a growth hormone secretagogue receptor into a cell under conditions so that growth hormone secretagogue receptor is expressed;

b) introducing a G-protein subunit into the cell;

c) introducing a detector molecule or a nucleic acid encoding a detector molecule into the cell, wherein the detector molecule is directly or indirectly responsive to a GHSR-ligand binding event;

d) contacting the cell with a compound suspected of being a growth hormone secretagogue; and e) determining whether the compound is a growth hormone secretagogue by monitoring the detector molecule.

BRIEF DESCRIPTION OF THE DRAWINGS

FIG. 1 is the DNA of Swine GHSR (Type I; SEQ ID NO: 1) contained in Clone 7-3.

FIG. 2 is the amino acid sequence (SEQ ID NO: 2) of swine GHSR encoded by the DNA of FIG. 1.

FIG. 3 is the entire open reading frame (SEQ ID NO: 3) of the Type I clone, of FIG. 1.

FIG. 4 is the DNA of Swine GHSR (Type II; SEQ ID NO: 4) contained in Clone 1375.

FIG. 5 is the amino acid sequence (SEQ ID NO: 5) of swine GHSR (Type II) encoded by the DNA of FIG. 4.

FIG. 6 is the DNA for human GHSR (Type I; SEQ ID NO: 6) contained in Clone 1146.

FIG. 7 is the amino acid sequence (SEQ ID NO: 7) of human GHSR (Type I) encoded by the DNA of FIG. 6.

FIG. 8 is the entire open reading frame (SEQ ID NO: 8) of Type I GHSR, encoded by DNA sequence of FIG. 6.

FIGS. 9A–B is the DNA for human GHSR (Type II; SEQ ID NO: 9) contained in Clone 1141.

FIG. 10 is the amino acid sequence (SEQ ID NO: 10) of human GHSR (Type II) encoded by Clone 1141.

FIG. 11 is the DNA for human GHSR (Type I; (SEQ ID NO: 11) contained in Clone 1143.

FIG. 12 is the amino acid sequence (SEQ ID NO: 12) of human GHSR (Type I) encoded by Clone 1143.

FIGS. 13A–B compares the ORF of swine Type I (lacking the MET initiator of the full length GHSR and lacking 12 additional amino acids) to the homologous domain of swine Type II receptors.

FIGS. 14A–B compares the homologous domain of human Type I and Type II receptors (the amino terminal sequence lacks the MET initiator and four additional amino acids).

FIG. 15 compares the ORFs of swine Type I and human Type I receptors (the amino terminal sequence lacks the MET initiator and 12 additional amino acids).

FIGS. 16A–B compares full length swine Type II and human Type II receptors.

FIG. 22 is the amino acid sequence (SEQ ID NO: 13) of the full length human GHSR (Type I) encoded by clone 11304.

FIGS. 27A–D is the rat GHSR DNA sequence (SEQ ID NO: 14) from the Met Initiation codon to the Stop codon. This sequence includes an intron.

FIGS. 28A–B is the open reading frame (SEQ ID NO: 15) only of the rat GHSR of FIGS. 27A–D.

FIG. 29 is the deduced amino acid sequence (SEQ ID NO: 16) of the ORF of FIGS. 28A–B.

Figure 17:
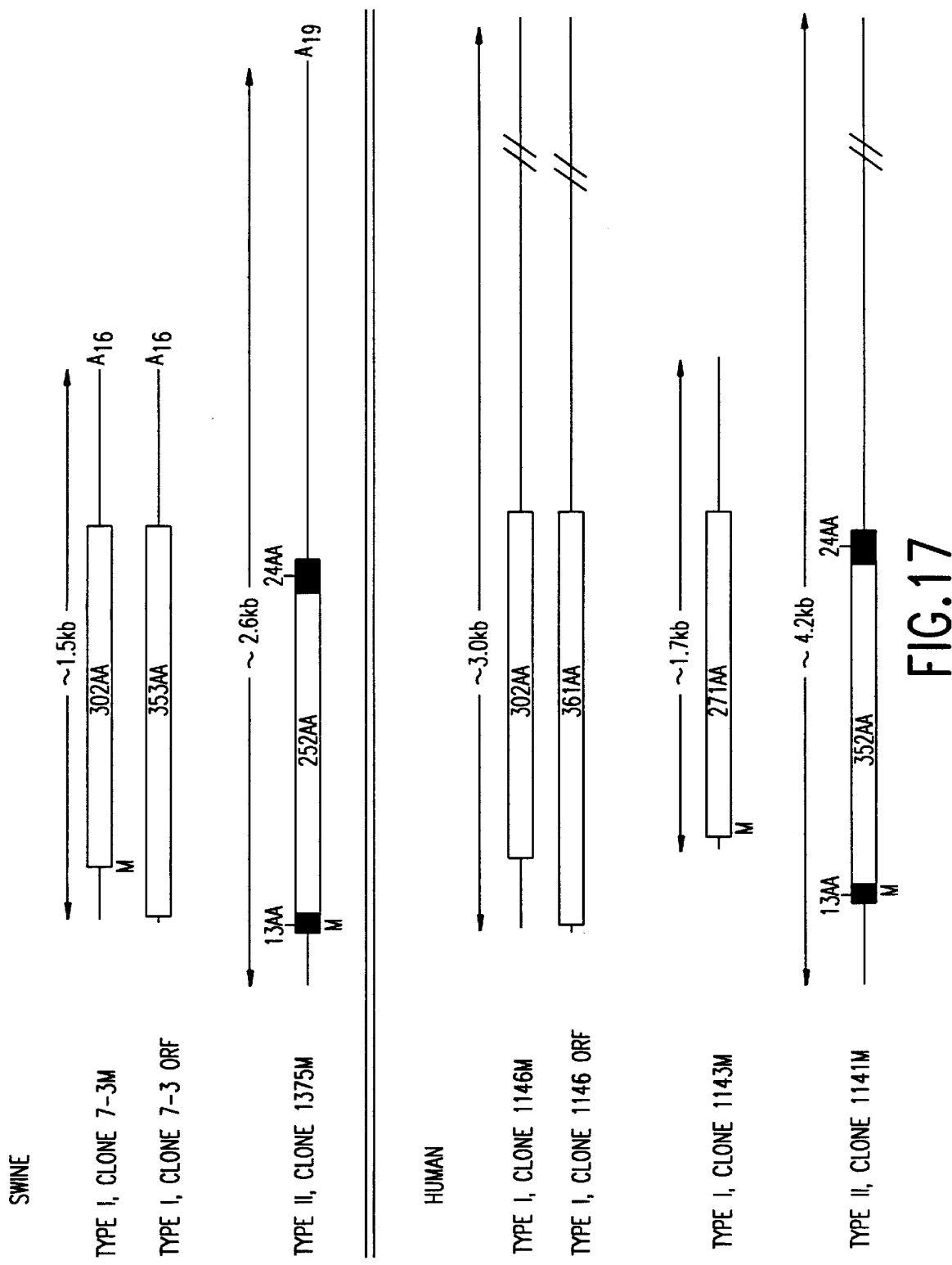
FIG. 17 Is a schematic diagram depicting the physical map of swine and human growth hormone secretagogue receptor cDNA clones.

As used throughout the specification and claims, the following definitions apply:

"Ligands" are any molecule which binds to a GHSR of this invention. Ligands can have either agonist, partial agonist, partial antagonist or antagonist activity.

"Growth hormone secretagogue" or "GHS" is any compound or agent that directly or indirectly stimulates or increases the release of growth hormone in an animal.

"Compound A" is (N-[1(R)-[1,2-dihydro-1-methanesulfonylspiro[3H-indole-3,4'-piperidin]-1'-yl)carbonyl]-2-(phenylmethyloxy)-ethyl]-2-amino-2-methyl-propanamide, described in Patchett et al, 1995 *Proc. Natl. Acad. Sci* 92: 7001–7005.

"Compound B" is (3-amino-3-methyl-N-(2,3,4.5-tetrahydro-2-oxo-1{2'-(1H-tetrazol-5-yl)(1,1'-biphenyl)-4-yl]-methyl}1H-1-benzazepin-3(R)yl-butanamide, described in Patchett et al, 1995 *Proc. Natl. Acad. Sci.* 92: 7001–7005.

This invention relates to assays for members of the growth hormone secretagogue receptor family of proteins, which includes growth hormone secretagogue receptors and growth hormone secretagogue related receptors. The growth hormone secretagogue receptor proteins, growth hormone receptor related proteins, nucleic acids encoding them and methods of making them using genetic engineering techniques are the subject of co-pending U.S. Provisional Patent Application Nos. 60/008,582, filed Dec. 13, 1995 and (Attorney Docket No. 19589PV2), filed herewith.

The proteins of this invention were found to have structural features which are typical of the 7-transmembrane domain (TM) containing G-protein linked receptor superfamily (GPC-R's or 7-TM receptors) receptors. Thus growth hormone secretagogue receptors make up new members of the GPC-R family of receptors. The intact receptors of this invention were found to have the general features of GPC-R's, including seven transmembrane regions, three intra- and extracellular loops, and the GPC-R protein signature sequence. The transmembrane domains and the GPC-receptor signature sequence are noted in the protein sequences of the Type I GHS receptor in FIGS. 3 and 8. Not all regions are required for functioning.

The GHSRs share some sequence homology with previously cloned GPC-receptors including the rat and human neurotensin receptor (approximately 32% identity) and the rat and human TRH receptor (approximately 30% identity).

The GHSRs were isolated and characterized using expression cloning techniques in Xenopus oocytes. The cloning was made difficult by three factors. First, prior to this invention, there was very little information available about both the biochemical characteristics, and the intracellular signaling/effector pathways of the proteins. Thus, cloning approaches which depend on the use of protein sequence information for the design of degenerate oligonucleotides to screen cDNA libraries or utilize the PCR could not be effectively utilized. Therefore, receptor bioactivity needed to be determined.

Secondly, the growth hormone secretagogue receptor does not occur in abundance—it is present on the cell membrane in about 10 fold less concentration than most other membrane receptors. In order to successfully clone the receptors, exhaustive precautions had be taken to ensure that the GHSR was represented in a cDNA library to be screened. This required: 1) isolation of intact, undegraded and pure poly(A)+ mRNA; 2) optimization of cDNA synthesis to maximize the production of full-length molecules; and 3) a library of larger size than normal needed to be screened (approximately 0.5 to 1×10$^7$ clones) to increase the probability that a functional cDNA clone may be obtained.

Thirdly, no permanent cell line which expresses these receptors is known. Therefore, primary pituitary tissue had to be used as a source for mRNA or protein. This is an added difficulty because most primary tissues express lower amounts of a given receptor than an immortalized cell line or tumor tissues. Further, the surgical removal of a pig pituitary and extraction of biologically active intact mRNA for the construction of a cDNA expression library is considerably more difficult than the extraction of mRNA from a tissue culture cell line. Along with the need to obtain fresh tissue continuously, there are problems associated with its intrinsic inter-animal and inter-preparation variability.

One aspect of this invention is directed to the development of an extremely sensitive, robust, reliable and high-throughput screening assay which could be used to identify portions of a cDNA library encoding the receptor.

The ability to identify cDNAs which encode growth hormone secretagogue receptors depended upon two discoveries made in accordance with this invention: 1) that growth hormone secretagogue receptor-ligand binding events are transduced through G proteins; and 2) that a particular G protein subunit, such as $G_{\alpha 11}$, must be present in the cells in order to detect receptor activity. Only when these two discoveries were made could an assay be devised to detect the presence of GHSR encoding DNA sequences.

Determination that GHSR is Distinct from the Growth Hormone Receptor

Figure 23A:
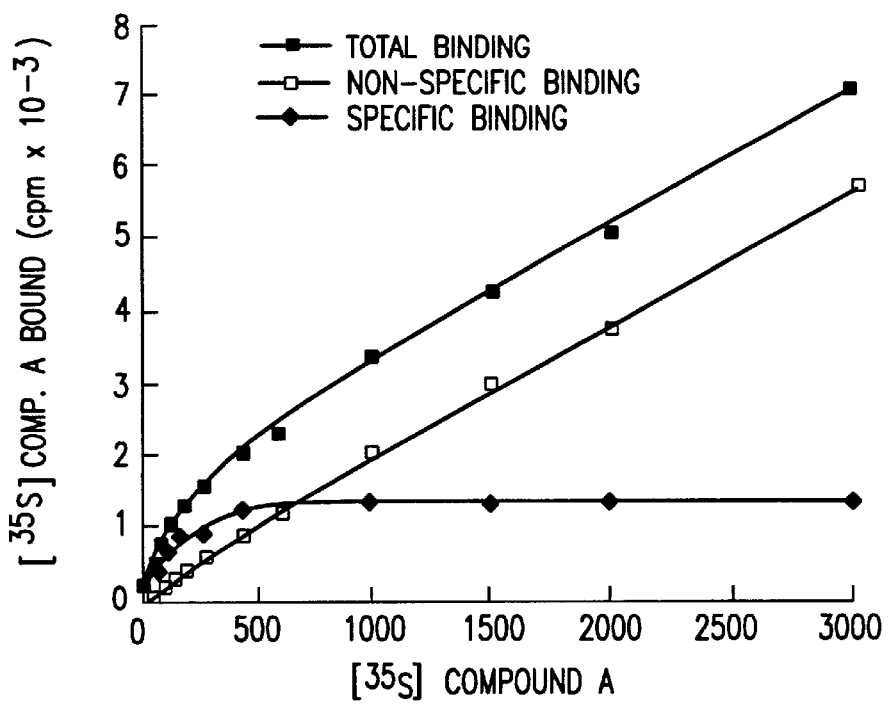
FIGS. 23A and 23B are graphs of measurement of [$^{35}$S]-Compound A binding to swine anterior pituitary membranes. 23A shows results of saturation experiments using a fixed amount of membrane. 23B shows saturation isotherms analyzed by Scatchard analysis.
Figure 23B:
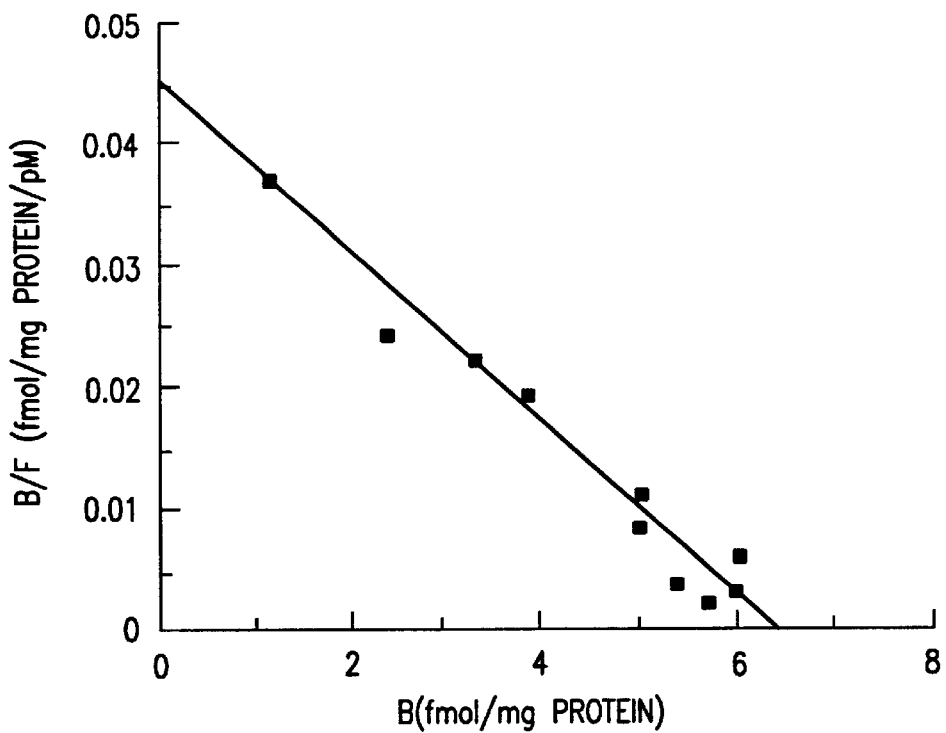

A radioreceptor assay using high specific activity (700–1, 100 Ci/mmole) [$^{35}$S]-labeled Compound A (a known GHS) as ligand was developed. Saturable, high affinity binding was detected in porcine anterior pituitary membranes (FIG. 23A). Scatchard analysis (FIG. 23B) indicated the presence of a single class of high affinity sites with an apparent dissociation constant ($K_D$) of 161±11 pM and a concentration ($B_{max}$) of 6.3±0.6 fmol/mg of protein (n=4). A similar specific high affinity binding was detected in rat pituitary membranes indicating a $K_D$ value of 180±9 pM and $B_{max}$ of 2.3±1.1 fmol/mg protein (n=3).

The high affinity binding to the GHSR makes up yet another aspect of this invention. This invention is also directed to a method of identifying novel GHSR proteins comprising labeling a known ligand, exposing it to a putative GHSR protein and determining if binding occurs.

Figure 24:
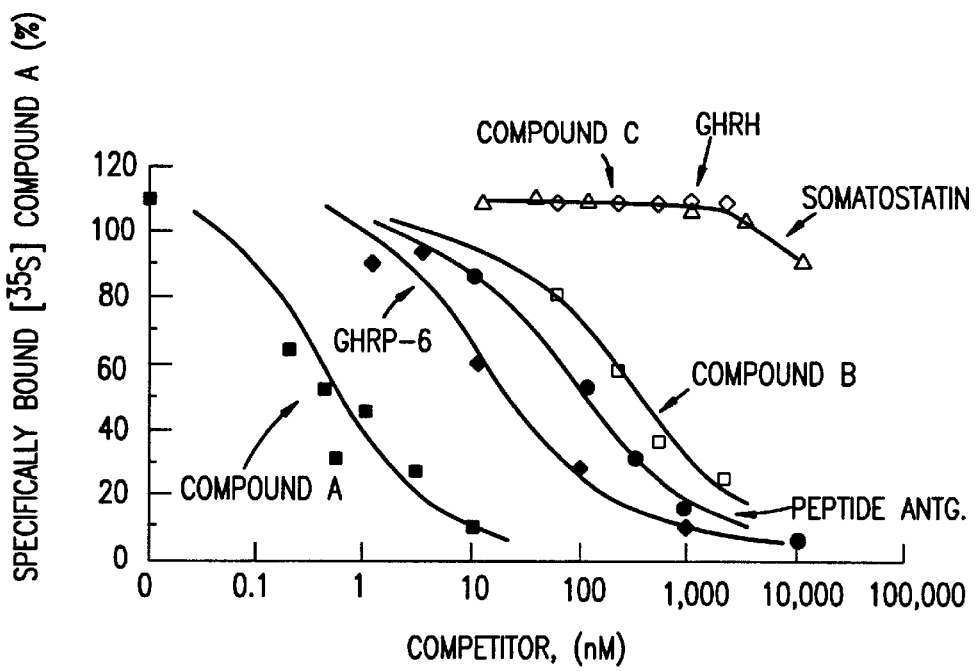
FIG. 24 shows the inhibition of [$^{35}$S]-Compound A binding to porcine anterior pituitary membranes by various compounds.
Figure 25:
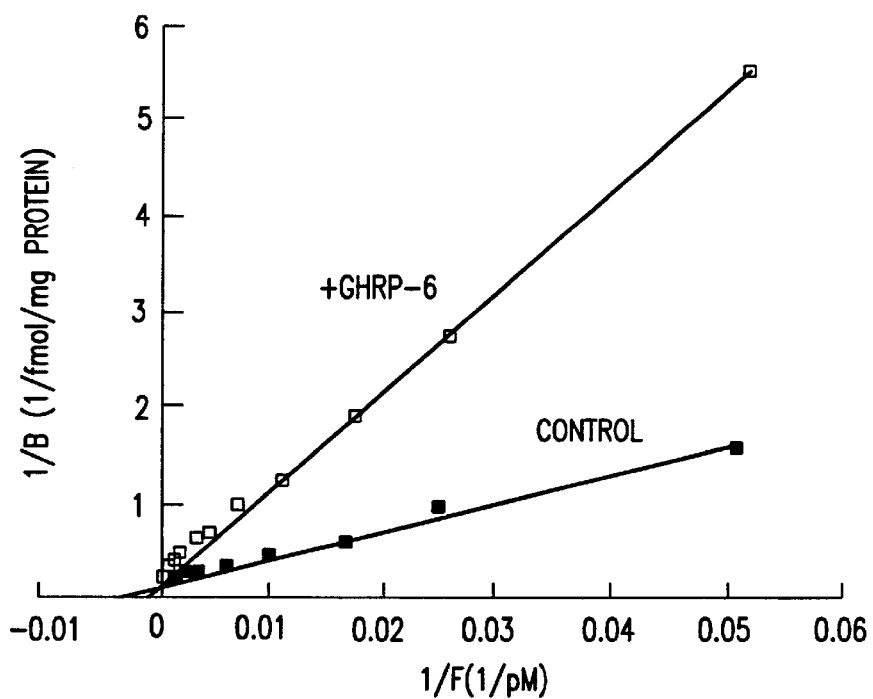
FIG. 25 shows the effect of GHRP-6 on specific [$^{35}$S]-Compound A binding to porcine anterior pituitary membranes at equilibrium.

The specificity of [$^{35}$S]-Compound A binding was established by determining the ability of GH secretagogues to compete with the radioligand for the binding sites (FIG. 24). Unlabeled Compound A completely displaced [$^{35}$S]-Compound A from specific binding sites with an inhibition constant, $K_i$, of 240 pM which is similar to the $K_D$ value determined by Scatchard analysis. Other GHSs, GHRP-6 ($K_i$ 6.3 nM), and peptide antagonist Compound B ($K_i$ 63 nM) had affinities of 3.8, 0.6 and 0.4%, respectively, of that of Compound A. Compound C, the biologically inactive stereoisomer of Compound B, competed poorly with [$^{35}$S]-Compound A binding. The saturation isotherm for [$^{35}$S]-Compound A binding analyzed by double reciprocal plot showed that GHRP-6 inhibition was overcome by increasing concentration of [$^{35}$S]-Compound A (FIG. 25). This result shows that GHRP-6 interacts competitively with Compound A in the same binding site. Similarly, Compound B was shown to be a competitor of [$^{35}$S]-Compound A binding. The most potent agonists had the highest affinities for pituitary receptor sites. Compounds which did not compete with [$^{35}$S]-Compound A at 1 µM included GHRH, somatostatin, met-enkephalin, substance P, galanin, gonadotropin releasing hormone, thyrotropin releasing hormone, gastrin releasing peptide, PHM-27, melanocyte stimulating hormone, pituitary adenylate cyclase activating polypeptide-38, phenoxybenzamine, dopamine, bromocriptine, methoxamine, benoxathian, isoproterenol, propanolol and clonidine.

A GHSRR gene may be identified by hybridizing a cDNA encoding a GHSR to a genomic DNA, under relaxed post-hybridizational washing conditions (6×SSC at 30° C.) or moderate post-hybridizational washing conditions (6×SSC at 45° C.). The hybridized area can be identified, isolated and the GHSRR can be cloned and the receptor expressed using conventional techniques.

Determination that GHSR is a G-Protein Receptor

Figure 26:
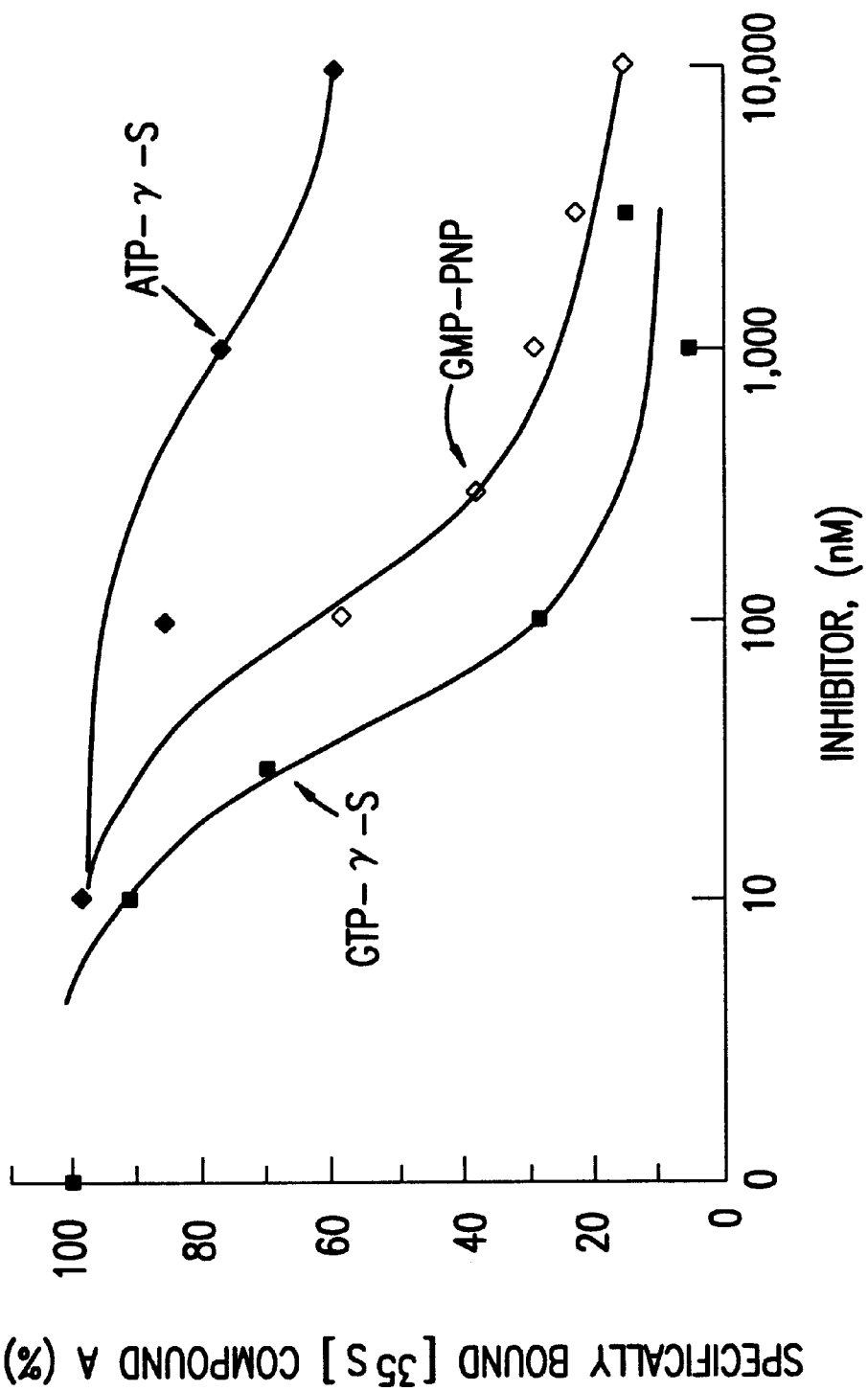
FIG. 26 shows the effects of GTP-γ-S and nucleotide on the specific [$^{35}$S]-Compound A binding to porcine anterior pituitary membranes.

To study whether the [$^{35}$S]-Compound A specific binding site was G-protein linked, the effects of stable GTP analogs GTP-γ-S and GMP-PNP on [$^{35}$S]-Compound A binding were studied. GTP-γ-S and GMP-PNP were found to be potent inhibitors of [$^{35}$S]-Compound A binding with IC$_{50}$ values of 30 and 110 nM, respectively (FIG. 26). ATP-γ-S was ineffective. In addition, in the absence of Mg$^{2+}$, only 15–25% of specific binding of [$^{35}$S]-Compound A binding was detected in comparison with control (10 mM Mg$^{2+}$) suggesting that the specific binding of [$^{35}$S]-Compound A required the presence of Mg$^{2+}$ regulate GH release in vivo) do not bind to the Compound A site. From these data, one can conclude that the receptor is G-protein linked.

When the GHSR is bound by ligand (a growth hormone secretagogue), the G-proteins present in the cell activate phosphatidylinositol-specific phospholipase C (PI-PLC), an enzyme which releases intracellular signaling molecules (diacylglycerol and inositol tri-phosphate), which in turn start a cascade of biochemical events that promote calcium mobilization. In accordance with this invention, detection of this biochemical cascade can be used as the basis of an assay.

Virtually any convenient eukaryotic cell may be used in the assay of this invention. These would include oocytes (preferred ones are from Xenopus sp.) but cell lines may be used as well as Examples of preferred cell lines are mammalian cell lines, including COS, HEK-293, CHO, HeLa, NS/0, CV-1, GC, GH3 and VERO.

One important component of the assay is a detector molecule. Preferably, the detector molecule is responsive to an intracellular event which is part of the biochemical cascade initiated by GHS-GHSR binding. One class of preferred detector molecules can respond to changes in calcium concentrations. A preferred detector molecule which responds to calcium concentrations is aequorin (a jellyfish photoprotein) which acts on the substrate coelenterazine. Other detector molecules include calcium chelators with fluorescence capabilities, such as FURA-2 and indo-1.

The detector molecule itself may be introduced into the cell, or nucleotides which encode the detector molecule may be introduced into the cell, under conditions which will allow the expression of the detector molecule. Generally, it is preferred to introduce nucleotides, such as DNA which encode the detector molecule into the cell, under conditions wherein the cell will express the detector molecule.

Heterotrimeric G proteins, consisting of α, β and γ subunits, serve to relay information from cell surface receptors to intracellular effectors, such as phospholipase C and adenylate cyclase. The G-protein alpha subunit is an essential component of the intracellular signal transduction pathway activated by receptor-ligand interaction. In the process of ligand-induced GPCR activation, the Gα subunit of a trimeric Gαβγ complex will exchange its bound GDP for GTP and dissociate from the βγ heterodimer. The dissociated Gα-protein serves as the active signal transducer, often in concert with the βγ complex, thus starting the activation of the intracellular signal transduction pathway. G-alpha subunits are classified into sub-families based on sequence identity and the main type of effectors are coupled: G$_s$, activate adenylate cyclase, G$_{i/o/t}$, inhibit adenylate cyclase Gq/11, activate PI-PLC, and G$_{12/13}$, effector unknown.

The expression of several receptors in heterologous cells has been shown to be increased by the co-expression of certain G$_α$ subunits. This observation formed the basis for the rationale to use G$_α$ subunits of several sub-families in conjunction with a source of GHSR (swine poly A$^+$ mRNA) to test if a GHS-induced functional response could be measured in the Xenopus oocyte system. GHS-induced responses were detected and were found to be strictly dependent on G$_{α11}$ co-expression, a unprecedented finding outlining the specificity of the interaction. The finding that the expression of the GPCR could be fully dependent on the addition of a single G-protein subunit was unexpected, since in all previously published work the addition of a G-protein subunit modulated an already existing activity. Here a previously absent signal was fully restored. This finding indicated that the lack of a signal in Xenopus eggs was fully dependent on a G-protein subunit as the limiting factor.

In conducting the assay, either the subunit itself or a nucleic acid encoding the subunit, or both may be added, and the addition events need not occur together.

Next, a nucleic acid or pool of nucleic acids, wherein at least one nucleic acid is suspected of encoding a GHSR or GHSRR is introduced into the cell. When trying to identify a possible GHSR or GHSRR gene from a large library, it is often more efficient to use a pool of nucleic acids, each nucleic acid being different from the other nucleic acids in the pool.

After the nucleic acid(s) suspected of encoding a GHSR or GHSRR is introduced into the cell, the cell is exposed to a known growth hormone secretagogue, such as Compound A (L-163,191). Any other growth hormone secretagogue may also be used. Preferred ones include: N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide, or 3-amino-3-methyl-N-(2,3,4,5-tetrahydro-2-oxo-1-{[2'-1H-tetrazol-5-yl)(1,1'-biphenyl)-4-yl]methyl}-1H-1-benzazepin-3(R)-yl-butanamide, or a compound disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,494,919; U.S. Pat. No. 5,494,920; U.S. Pat. No. 5,492,916; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; PCT Patent Pub. No. WO 95/34311; PCT Patent Pub. No. WO 96/02530; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995), or any other growth hormone secretagogue.

If one or more of the nucleic acids does encode a GHSR, or GHSRR, then the secretagogue ligand will bind the receptor, G-protein will be activated, the calcium level will fluctuate, and the detector molecule will change so that it can be monitored. For the system using aequorin and coelenterazine, receptor-GHS binding will produce measurable bioluminescence.

If the procedure used a complex pool of nucleic acids, one or more of which may encode the receptor, then further screening will be necessary to determine which nucleic acid is responsible for encoding GHSR or GHSRR. Once a positive result is found, the procedure can be repeated with a sub-division of the nucleic acid pool (for example, starting with approximately 10,000 nucleic acids, then using approximately 1,000, then approximately 500, then approximately 50, and then pure). In this procedure, RNA pools are preferred.

Using this general protocol in Xenopus oocytes with a swine cDNA expression library, Clone 7-3 was identified as containing nucleic acid encoding a swine growth hormone secretagogue receptor. The clone is approximately 1.5 kb in size, and downstream from the presumed initiator methionine (MET), contains an open reading frame (ORF) encoding 302 amino acids ($M_r$=34,516). The DNA and deduced amino acid sequence is given in FIGS. 1 and 2. When hydropathy analysis (e.g. Kyte-Doolittle; Eisenberg, Schwartz, Komaron and Wall) is performed on the protein sequence of clone 7-3, only 6 predicted transmembrane domains are present downstream of the presumed MET initiator. However, translation of the longest ORF encoded in clone 7-3 encodes a protein of 353 amino acids ($M_r$=39,787), but is devoid of an apparent initiator MET (FIG. 3). Seven transmembrane segments are encoded in the longer, 353 amino acid protein in which a MET translation initiation codon located upstream of TM1 is absent (FIG. 3). Thus, clone 7-3 appears truncated at its amino terminus, but is fully functional, demonstrating that clone 7-3 is a functional equivalent of a native GHSR.

The resultant cDNA clone (or shorter portions of for instance only 15 nucleotides long) may be used to probe libraries under hybridization conditions to find other receptors which are similar enough so that the nucleic acids can hybridize, and is particularly useful for screening libraries from other species. Using this procedure, additional human, swine and rat GHSR cDNAs have been cloned and their nucleotide sequence determined. In this step, one of ordinary skill in the art will appreciate that the hybridization conditions can vary from very stringent to relaxed. Proper temperature, salt concentrations, and buffers are well known. As used herein, "standard post hybridizational washing" conditions mean 6×SSC at 55° C. "Relaxed post hybridizational washing" conditions means 6×SSC at 30° C.

A swine pituitary library, a human pituitary library, and a rat pituitary library were hybridized with a radiolabeled cDNA derived from the open reading frame of the swine GHSR clone 7-3. Twenty one positive human GHSR cDNA clones were isolated and five swine library pools yielded a strong hybridization signal and contained clones with inserts larger than clone 7-3, as judged from their insert size on Southern blots. A single rat cDNA clone was also isolated.

Nucleotide sequence analysis revealed two types of cDNAs for both the human and swine GHSR cDNAs. The first (Type I) encodes a protein represented by clone 7-3, encoding 7-TM domains (the amino acid sequence of a full length human clone 11304 is shown in FIG. 22). The full length open reading frame extends 13 amino acids beyond the largest predicted open reading frame of clone 7-3, (353 amino acids).

The second (type II) diverges in its nucleotide sequence from the type I cDNA at its 3'-end, at the second predicted amino acid of TM-6. In the type II cDNAs, TM-6 is truncated and fused to a short contiguous reading frame of only 24 amino acids, followed by a translation stop codon. Swine clone 1375 is an example of a Type II cDNA (FIGS. 4 and 5). These 24 amino acids beyond TM-6 are highly conserved when compared between human and swine cDNAs. The DNA and amino acid sequences of the human GHSR Type I and II are given in FIGS. 6–12 and 22. A predicted full length cDNA encoding the human Type I receptor, that is, a molecule encoding 7-TM domains with an initiator MET in a favorable context preceded by an inframe termination codon is isolated, and termed clone 11304. The predicted ORF of clone 11304 for the full length Type I GHSR measures 366 amino acids ($M_r$=41,198; FIG. 22). A full length human Type II cDNA encodes a polypeptide of 289 amino acids ($M_r$=32,156; FIGS. 9A–B and 10). Sequence alignments performed at both the nucleic acid and protein levels show that Type I and II GHSR's are highly related to each other and across species (FIGS. 13–16). The human and swine GHSR sequences are 93% identical and 98% similar at the amino acid level.

The nucleotide sequence encoding the missing amino terminal extension of swine Type I clone 7-3 is derived from the full length human Type I clone as well as the human and swine Type II cDNAs. The reading frame of the full length clones extended 13 amino acids beyond the amino terminal sequence of clone 7-3 and this sequence was conserved in 12/13 amino acid residues when compared between human and swine. The amino terminal extension includes a translation initiator methionine in a favorable context according to Kosak's rule, with the reading frame further upstream being interrupted by a stop codon. A schematic physical map of Type I and II swine and human cDNA clones is given in FIG. 17.

The rat clone was also further investigated. Sequence analysis revealed the presence of a non-coding intronic sequence at nt 790 corresponding to a splice-donor site (see FIGS. 27A–D, 28A–B, and 29.) The G/GT splice-donor site occurs two amino acids after the completion of the predicted transmembrane domain 5 (leucine 263), thus dividing the rat GHSR into an amino-terminal segment (containing the extra cellular domain, TM-1 through TM-5, and the first two intra- and extra-cellular loops) and a carboxy-terminal segment (containing TM-6, TM-7, the third intra- and extra- cellular loops, and the intra-cellular domain). The point of insertion and flanking DNA sequences are highly conserved, and also present in both human and swine Type I and II cDNAs.

Comparison of the complete open reading frame encoding the rat GHSR protein to human and swine homologs reveals a high degree of sequence identity (rat vs. human, 95.1%; rat vs. swine 93.4%).

Human and swine Type 1 cRNAs expressed in oocytes were functional and responded to concentrations Compound A ranging from 1 µM to as low as 0.1 nM in the aequorin bioluminescence assay. Human or swine Type II-derived cRNAs that are truncated in TM-6 failed to give a response when injected into oocytes and these represent a receptor subtype which may bind the GHS, but cannot effectively activate the intracellular signal transduction pathway. In addition the Type II receptor may interact with other proteins and thus reconstitute a functional GHSR. Proteins such as these which may have ligand-binding activity, but are not active in signal transduction are particularly useful for ligand-binding assays. In these cases, one may also overexpress a mutant protein on the cell membrane and test the binding abilities of putative labeled ligands. By using a non-signaling mutant which is constitutively in a high affinity state, binding can be measured, but no adverse metabolic consequences would result. Thus use of non-signaling mutants are an important aspect of this invention.

Figures 18, 19:
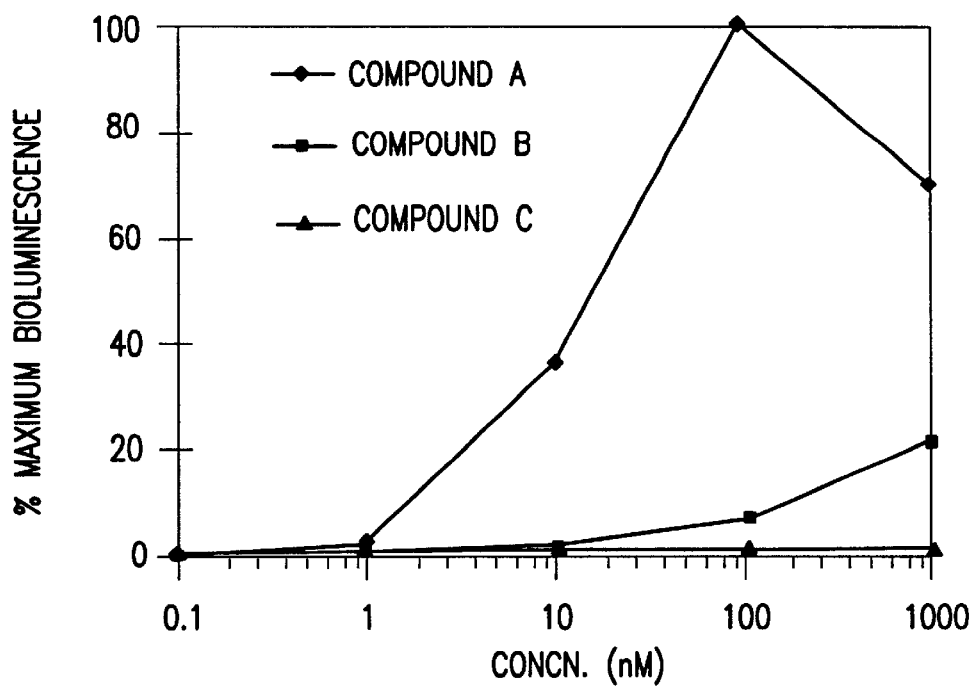
FIG. 18 is a graph demonstrating the pharmacology of the expressed swine and human growth hormone secretagogue receptors in Xenopus oocytes using the aequorin bioluminescence assay.
FIG. 19 is a table demonstrating the pharmacology of the expressed swine and human growth hormone secretagogue receptors in Xenopus oocytes using the aequorin bioluminescence assay and various secretagogues.
Figures 20, 21:
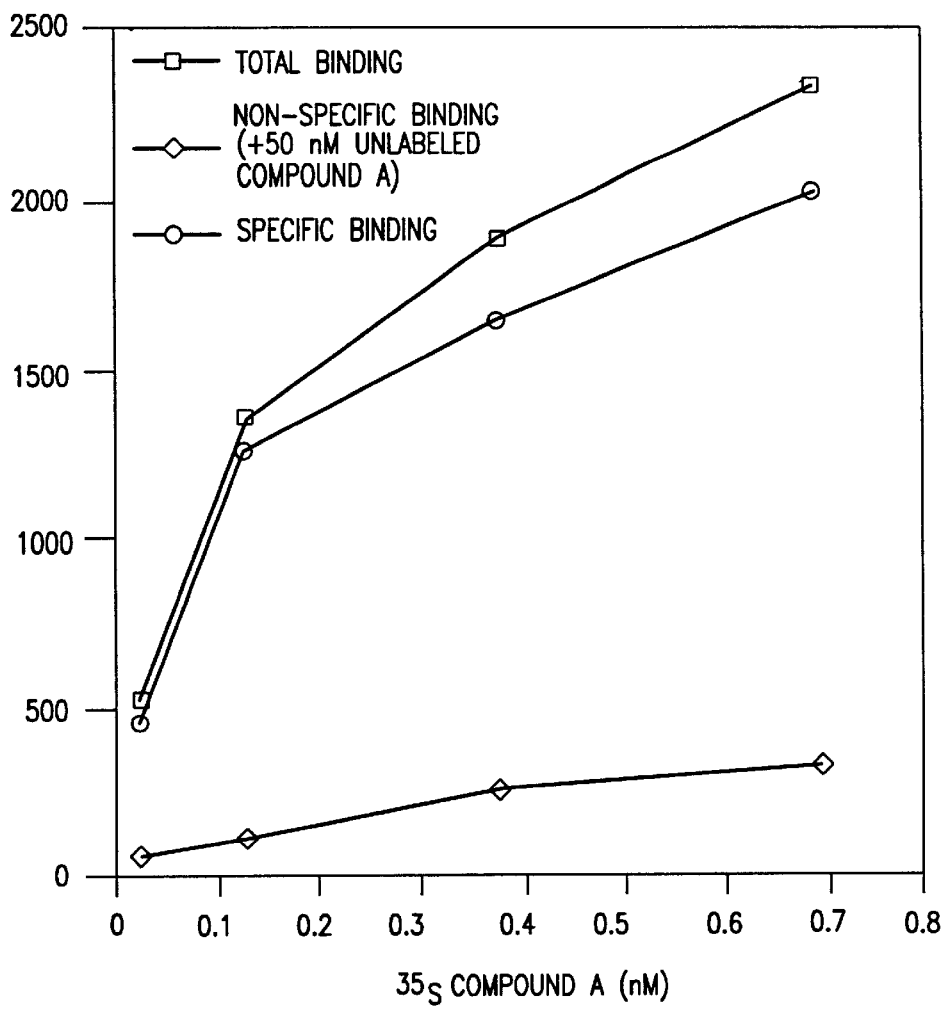
FIG. 20 is a graph representing the pharmacology of the pure expressed swine growth hormone secretagogue receptor in COS-7 cells using the $^{35}$S-labeled Compound A binding assay.
FIG. 21 is a table representing the competition analysis with the pure expressed swine growth hormone secretagogue receptor in COS-7 cells using the $^{35}$S-labeled Compound A binding assay and various secretagogues and other G-protein coupled-receptors (GPC-receptors) ligands in a competition assay.
Figure 30:
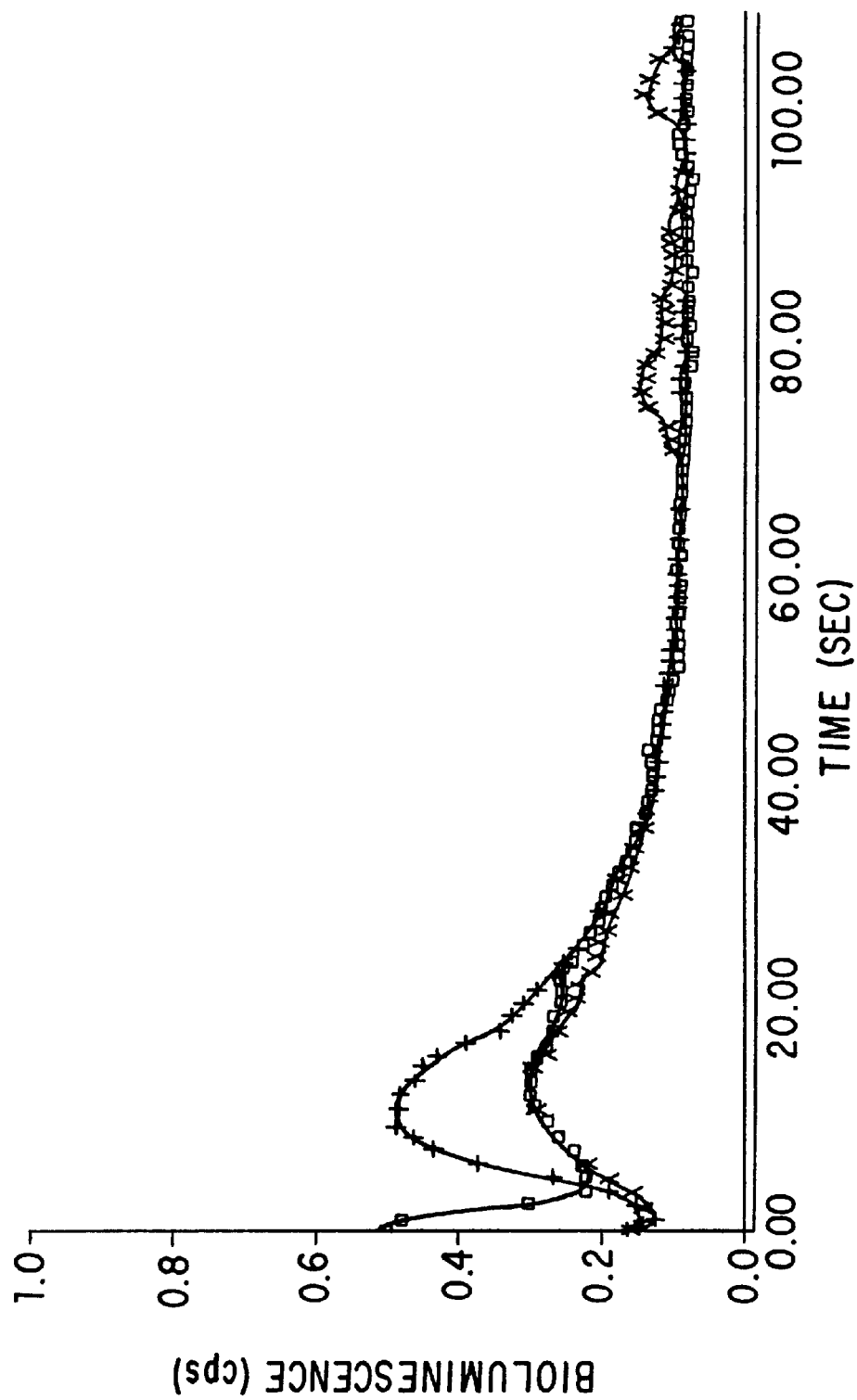
FIG. 30 shows expression of functional rat GHSR in transfected HEK-293 cells.

The pharmacological characterization of human Type I, swine Type I and rat receptors in the aequorin bioluminescence assay in oocytes is summarized in FIGS. 18, 19 and 30. Peptidyl and non-peptidyl bioactive GHS's were active in a similar rank order of potency as observed for the native pituitary receptor. Independent confirmatory evidence that the Type I GHSR (shown for swine clone 7-3) encodes a fully-functional GHSR is given by the finding that when clone 7-3 is expressed transiently in mammalian COS-7 cells, high affinity (KD~0.2 nM), saturable ($B_{max}$~80 fmol/mg protein) and specific binding (>90% displaced by 50 nM unlabeled Compound A) is observed for $^{35}$S-Compound A (FIGS. 20–21).

By varying the parameters of the above assays, one can search for other unknowns. For example, in the assay which detects whether a nucleic acid which encodes a GHSR or GHSRR is present, one can modify the assay so that it detects whether a GHS is present. In this embodiment, a nucleic acid encoding GHSR or GHSRR is introduced into the cell, as well as a nucleic acid encoding a detector molecule, and a G protein subunit. The cell is contacted with at least one compound which is a putative GHS. If the compound is a GHS, then the GHS will bind the GHSR or GHSRR, and the resultant intracellular events can be detected by monitoring the detector molecule. If the compound is not a GHS, then no such activity will be detected. This GHS assay forms yet another aspect of this invention.

A further aspect of this invention are novel ligands which are identified using the above assay.

Expression of several receptors in heterologous cells has been shown to be increased by the co-expression of certain $G_\alpha$ subunits. This observation formed the basis for the rationale to the use of $G_\alpha$ subunits of several subfamilies in conjunction with a source of GHSR (swine poly[A$^+$]mRNA) to test if a GHS-induced functional response could be measured in the Xenopus oocyte system. GHS-induced responses were detected and were found to be strictly dependent on $G_{\alpha 11}$ co-expression, an unprecedented finding outlining the specificity of the interaction. Thus another aspect of this invention is a method of detecting a GHS response comprising co-expressing a $G_{\alpha 11}$ protein subunit in a cell also expressing a GHSR, exposing the cell to a GHS, and detecting the response.

The presence of $G_{\alpha 11}$ was essential in using poly A+ RNA or complex cRNA pools (i.e. 10.000 cRNAs). However, once a pure clone was obtained the requirement for the G-protein addition was no longer essential. This indicates that the need for G-protein addition depended on the purity of the nucleic acid, the most sensitive assay requiring $G\alpha$ subunit addition. Thus another aspect of this invention is a method of determining the presence of an nucleic acid which encodes a growth hormone secretagogue receptor or growth hormone secretagogue related receptor comprising:

a) introducing a nucleic acid suspected of encoding a GHSR or GHSRR into a cell which does not naturally express the receptor on its cell membrane;

b) introducing a detector molecule or a nucleic acid encoding a detector molecule into the cell, wherein the detector molecule is directly or indirectly responsive to a receptor-ligand binding event;

c) contacting the cell with a growth hormone secretagogue; and d) determining whether the nucleic acid encodes a receptor by monitoring the detector molecule.

Similarly, another aspect of this invention is an assay method to determine the presence of a growth hormone secretagogue comprising:

a) introducing a nucleic acid which encodes a growth hormone secretagogue receptor into a cell under conditions so that growth hormone secretagogue receptor is expressed;

b) introducing a detector molecule or a nucleic acid encoding a detector molecule into the cell, wherein the detector molecule is directly or indirectly responsive to a GHSR-ligand binding event;

c) contacting the cell with a compound suspected of being a growth hormone secretagogue; and d) determining whether the compound is a growth hormone secretagogue by monitoring the detector molecule.

Ligands detected using assays described herein may be used in the treatment of conditions which occur when there is a shortage of growth hormone, such as observed in growth hormone deficient children, elderly patients with musculoskeletal impairment and recovering from hip fracture, patients with neurodegenerative diseases, and patients recovering from coronary by-pass surgery, and osteoporosis.

A GHS receptor, preferably imobilized on a solid support, may be used diagnostically for the determination of the concentration of growth hormone secretagogues, or metabolites thereof, in physiological fluids, e.g., body fluids, including serum, and tissue extracts, as for example in patients who are undergoing therapy with a growth hormone secretagogue.

The administration of a GHS receptor to a patient may also be employed for purposes of: amplifying the net effect of a growth hormone secretagogue by providing increased downstream signal following administration of the growth hormone secretagogue thereby diminishing the required dosage of growth hormone secretagogue; or diminishing the effect of an overdosage of a growth hormone secretagogue during therapy.

The following non-limiting Examples are presented to better illustrate the invention.

EXAMPLE 1

Preparation of High Specific Activity Radioligand [$^{35}$S]-Compound A

[$^{35}$S]-Compound A was prepared from an appropriate precursor, N-[1(R)-[(1,2-dihydrospiro[3H-indole-3,4'-piperidin]-1'-yl)-carbonyl]-2-(phenyl-methyloxy)ethyl]-2-amino-t-butoxycarbonyl-2-methylpropanamide, using methane [$^{35}$S]sulfonyl chloride as described in Dean DC, et al., 1995, In: Allen J, Voges R (eds) *Synthesis and Applications of Isotopically Labelled Compounds,* John Wiley & Sons, New York, pp. 795–801, Purification by semi-preparative HPLC (Zorbax SB-phenyl column, 68% MeOH/water, 0.1% TFA, 5 ml/min) was followed by N-t-BOC cleavage using 15% trifluroacetic acid in dichloromethane (25° C., 3 hr) to give [methylsulfonyl-$^{35}$S]Compound A in near quantitative yield. HPLC purification (Hamilton PRP-1 4.6×250 mm column, linear gradient of 50–75% methanol-water with 1 mM HCl over 30 min, 1.3 ml/min) provided the ligand in >99% radiochemical purity. The structure was established by HPLC coelution with unlabeled Compound A and by mass spectral analysis. The latter method also indicated a specific activity of ~1000 Ci/mmol.

EXAMPLE 2

Preparation of Pituitary Membranes

Frozen anterior pituitary glands from male swine (50–80 Kg) or from the Wistar male rats (150–200 g) were homogenized in a tissue homogenizer in ice-cold buffer (50 mM Tris-HCl buffer, pH 7.4, 5 mM $MgCl_2$, 2.5 mM EDTA, 0.1% bovine serum albumin and 30 µg/ml bacitracin). The homogenates were centrifuged for 5 min at 1,400×g and the resulting supernatants were then centrifuged at 34,000×g for 20 min. The pellets were resuspended in same buffer to a 1,500 µg protein/ml and stored at −80° C. Protein was determined by a Bio-Rad method (Bio-Rad Laboratories, Richmond, Calif.).

EXAMPLE 3

Receptor Binding Assay

The standard binding solution contained: 400 m of 25 mM Tris-HCl buffer, pH 7.4, 10 mM $MgCl_2$, 2.5 mM EDTA, and 100 pM [$^{35}$S]-Compound A. Pituitary membranes (100 µl, 150 µg protein) were added to initiate the binding reaction. Aliquots were incubated at 20° C. for 60 min and bound radioligand was separated from free by filtration through GF/C filters pretreated with 0.5% of polyethylenimine in a Brandel cell harvester. The filters were washed three times with 3-ml of ice-cold buffer (50 mM Tris-HCl, pH 7.4, 10 mM $MgCl_2$, 2.5 mM EDTA and 0.015% Triton X-100) and the radioactivity on the filters were counted in Aquasol 2. Specific binding was defined as the difference between total binding and nonspecific binding assayed in 500 nM unlabeled Compound A. Specific bindings were 65–85 and 45–60% of total binding, in porcine and rat membranes, respectively. Assays were carried out in triplicate and experiments repeated at least three times.

EXAMPLE 4

Oocyte Preparation and Selection

*Xenopus laevis* oocytes were isolated and injected using standard methods previously described by Arena, et. al. 1991, *Mol. Pharmacol.* 40, 368–374, which is hereby incorporated by reference. Adult female *Xenopus Laevis* frogs (purchased from Xenopus One, Ann Arbor, Mich.) were anesthetized with 0.17% tricaine methanesulfonate and the ovaries were surgically removed and placed in a 60 mm culture dish (Falcon) containing OR-2 medium without calcium (82.5 mM NaCl, 2 mM KCl, 2.5 mM sodium pyruvate, 1 mM $MgCl_2$, 100 µ/ml penicillin, 1 mg/ml streptomycin, 5 mM HEPES, pH=7.5; ND-96 from Specialty Media, NJ). Ovarian lobes were broken open, rinsed several times, and oocytes were released from their sacs by collagenase A digestion (Boehringer-Mannheim; 0.2% for 2–3 hours at 18° C.) in calcium-free OR-2. When approximately 50% of the follicular layers were removed, Stage V and VI oocytes were selected and placed in ND-86 with calcium (86 mM NaCl, 2 mM KCl, 1 mM $MgCl_2$, 1.8 mM $CaCl_2$, 2.5 mM sodium pyruvate, 0.5 mM theopylline, 0.1 mM gentamycin, 5 mM HEPES [pH=7.5]). For each round of injection, typically 3–5 frogs were pre-tested for their ability to express a control G-protein linked receptor (human gonadotropin-releasing hormone receptor) and show a robust phospholipase C intracellular signaling pathway (incubation with 1% chicken serum which promotes calcium mobilization by activation of phospholipase C). Based on these results, 1–2 frogs were chosen for library pool injection (50 nl of cRNA at a concentration of 25 ng (complex pools) to 0.5 ng (pure clone) per oocyte usually 24 to 48 hours following oocyte isolation.

EXAMPLE 5 mRNA Isolation

Total RNA from swine (50–80 kg, Yorkshire strain) pituitaries (snap-frozen in liquid nitrogen within 1–2 minutes of animal sacrifice) was prepared by a modified phenol:guanidinium thiocyanate procedure (Chomczynski, et al, 1987 *Anal. Biochem.* 162, 156–159, which is hereby incorporated by reference), using the TRI-Reagent LS as per the manufacturer's instructions (Molecular Research Center, Cincinnati, Ohio). Typically, 5 mg of total RNA was obtained from 3.5 g wet weight of pituitary tissue. Poly $(A)^+$ RNA was isolated from total RNA by column chromatography (two passes) on oligo (dT) cellulose (Pharmacia, Piscataway, N.J.). The yield of poly $(A)^+$ mRNA from total RNA was usually 0.5%. RNA from other tissues was isolated similarly.

EXAMPLE 6 cDNA Library Construction

First-strand cDNA was synthesized from poly $(A)^+$ mRNA using M-MLV RNAse (−) reverse transcriptase (Superscript, GIBCO-BRL, Gaithersberg, Md.) as per the manufacturer's instructions with an oligo (dT)/Not I primer-adapter. Following second-strand cDNA synthesis, double-stranded cDNA was subjected to the following steps: 1) ligation to EcoR I adapters, 2) Not I digestion, and 3) enrichment for large cDNAs and removal of excess adapters by gel filtration chromatography on a Sephacryl S-500 column (Pharmacia). Fractions corresponding to high molecular weight cDNA were ligated to EcoR I/Not I digested pSV-7, a eucaryotic expression vector capable of expressing cloned cDNA in mammalian cells by transfection (driven by SV-40 promoter) and in oocytes using in vitro transcripts (initiated from the T7 RNA polymerase promoter). pSV-7 was constructed by replacing the multiple cloning site in pSG-5 (Stratagene, La Jolla, Calif.; Green, S. et al, 1988 *Nucleic Acids Res.* 16:369, which is hereby incorporated by reference) with an expanded multiple cloning site. Ligated vector:cDNA was transformed into *E. coli* strain DH10B (GIBCO-BRL) by electroporation with a transformation efficiency of 1 ×$10^6$ pfu/10 ng double-stranded cDNA. The library contained approximately 3×$10^6$ independent clones with greater than 95% having inserts with an average size approximating 1.65 kb (range 0.8–2.8 kb). Unamplified library stocks were frozen in glycerol at −70° C. until needed. Aliquots of the library were amplified once prior to screening by a modification of a solid-state method (Kriegler, M. in *Gene Transfer and Expression: A Laboratory Manual* Stockton Press, NY 1990). Library stocks were titered on LB plates and then the equivalent of 500–1000 colonies was added to 13 ml of 2×YT media containing 0.3% agarose and 100 µg/ml carbenicillin in a 14 ml round-bottom polypropylene tube (Falcon). The bacterial suspension was chilled in a wet ice bath for 1 hour to solidify the suspension, and then grown upright at 37° C. for 24 hrs. The resultant bacterial colonies were harvested by centrifugation at 2000×g at RT for 10 min, resuspended in 3 ml 2×YT/carbenicillin. Aliquots were taken for frozen stocks (5%) and plasmid DNA preparation.

EXAMPLE 7

Plasmid DNA Preparation and cRNA Transcription

Plasmid DNA was purified from pellets of solid-state grown bacteria (1000 pools of 500 independent clones each) using the Wizard Miniprep kit according to the manufacturer's instructions (Promega Biotech, Madison, Wis.). The yield of plasmid DNA from a 14 ml solid-state amplification was 5–10 µg. In preparation for cRNA synthesis, 4 µg of DNA was digested with Not I, and the subsequent linearized DNA was made protein and RNase-free by proteinase K treatment (10 μg for 1 hour at 37° C.), followed by two phenol, two chloroform/isoamyl alcohol extractions, and two ethanol precipitations. The DNA was resuspended in approximately 15 μl of RNase-free water and stored at −70° C. until needed. cRNA was synthesized using a kit from Promega Biotech with modifications. Each 50 μl reaction contained: 5 μl of linearized plasmid (approximately 1 μg), 40 mM Tris-HCl (pH=7.5), 6 mM MgCl$_2$, 2 mM spermidine, 10 mM NaCl, 10 mM DTT, 0.05 mg/ml bovine serum albumin, 2 units/ml RNasin, 800 μM each of ATP, CTP and UTP, 200 μM GTP, 800 μM m7G(5')ppp(5')G, 80 units of T7 RNA polymerase, and approximately 20,000 cpm of $^{32}$P-CTP as a trace for quantitation of synthesized RNA by TCA precipitation. The reaction was incubated for 3 hrs. at 30° C.; 20 units of RNase-free DNase was added, and the incubation was allowed to proceed for an additional 15 min. at 37° C. cRNA was purified by two phenol, chloroform/isoamyl alcohol extractions, two ethanol precipitations, and resuspended at a concentration of 500 ng/ml in RNase-free water immediately before use.

EXAMPLE 8

Aequorin Bioluminescence Assay (ABA) and Clone Identification

The ABA requires injection of library pool cRNA (25 ng/egg for pool sizes of 500 to 10,000) with aequorin cRNA (2 ng/egg) supplemented with the G-protein alpha subunit G$_{\alpha 11}$ (2 ng/egg). To facilitate stabilization of synthetic transcripts from aequorin and G$_{\alpha 11}$ plasmids, the expression vector pCDNA-3 was modified (termed pcDNA-3v2) by insertion (in the Apa I restriction enzyme site of the polylinker) of a cassette to append a poly (A) tract on all cRNA's which initiate from the T7 RNA polymerase promoter. This cassette includes (5' to 3'): a Bgl II site, pA (20) and a Sfi I site which can be used for plasmid linearization. Polymerase chain reaction (PCR) was utilized to generate a DNA fragment corresponding to the open reading frame (ORF) of the aequorin cDNA with an optimized Kosak translational initiation sequence (Inouye, S. et. al., 1985, *Proc. Natl. Acad. Sci. USA* 82:3154–3158). This DNA was ligated into pCDNA-3v2 linearized with EcoR I and Kpn I in the EcoR I/Kpn I site of pCDNA-3v2. G$_{\alpha 11}$ cDNA was excised as a CIa I/Not I fragment from the pCMV-5 vector (Woon, C. et. al., 1989 *J. Biol. Chem.* 264: 5687–93), made blunt with Klenow DNA polymerase and inserted into the EcoR V site of pcDNA-3v2. cRNA was injected into oocytes using the motorized "Nanoject" injector (Drummond Sci. Co., Broomall, Pa.) in a volume of 50 nl. Injection needles were pulled in a single step using a Flaming/Brown micropipette puller, Model P-87 (Sutter Instrument Co) and the tips were broken using 53×magnification such that an acute angle was generated with the outside diameter of the needle being <3 μm. Following injection, oocytes were incubated in ND-96 medium, with gentle orbital shaking at 18° C. in the dark. Oocytes were incubated for 24 to 48 hours (depending on the experiment and the time required for expression of the heterologous RNA) before "charging" the expressed aequorin with the essential chromophore coelenterazine. Oocytes were "charged" with coelenterazine by transferring them into 35 mm dishes containing 3 ml charging medium and incubating for 2–3 hours with gentle orbital shaking in the dark at 18° C. The charging medium contained 10 μM coelenterazine (Molecular Probes, Inc., Eugene, Oreg.) and 30 μM reduced glutathione in OR-2 media (no calcium). Oocytes were then returned to ND-86 medium with calcium medium described above and incubation continued in the dark with orbital shaking until bioluminescence measurements were initiated. Measurement of GHSR expression in oocytes was performed using a Berthold Luminometer LB953 (Wallac Inc., Gaithersburg, Md.) connected to a PC running the Autolumat-PC Control software (Wallac Inc., Gaithersburg, Md.). Oocytes (singly or in pairs) were transferred to plastic tubes (75×12 mm, Sarstedt) containing 2.9 ml Ca$^{++}$-free OR-2 medium. Each cRNA pool was tested using a minimum of 3 tubes containing oocytes. Bioluminescence measurements were triggered by the injection of 0.1 ml of 30 μM Compound A (1 μM final concentration) and recordings were followed for 2 min. to observe kinetic responses consistent with an IP$_3$-mediated response.

Pool S10–20 was prepared from the unfractionated swine pituitary cDNA library and was composed of 10 pools each of 1000 clones. S10–20 gave a positive signal on two luminometer instruments and the component pools were then individually tested for activity. From the 10 pools of 1000 clones, only pool S271 gave a positive response. This pool was made from two pools of 500 clones designated P541 and P542. Again, only one of the pools, P541, gave a positive bioluminescent signal in the presence of 1 μM Compound A. At this point, the bacterial titer was determined in the glycerol stock of P541 such that dilutions could be plated onto LB agar plates containing 100 μg/ml carbenicillin to yield approximately 50 colonies per plate. A total of 1527 colonies were picked and replicated from 34 plates. The colonies on the original plates were then washed off, plasmids isolated, cRNA synthesized and injected into oocytes. cRNA prepared from 8 of the 34 plates gave positive signals in oocytes. Two plates were selected and the individual colonies from these plates were grown up, plasmid isolated, cRNA prepared and injected into oocytes. A single clonal isolate from each plate (designated as clones 7-3 and 28-18) gave a positive bioluminescence response to 1 μM Compound A. Clone 7-3 was further characterized.

EXAMPLE 9

Receptor Characterization

DNA sequencing was performed on both strands using an automated Applied Biosystems instrument (ABI model 373) and manually by the dideoxy chain termination method using Sequenase II (US Biochemical, Cleveland, Ohio). Database searches (Genbank 88, EMBL 42, Swiss-Prot 31, PIR 40, dEST, Prosite, dbGPCR), sequence alignments and analysis of the GHSR nucleotide and protein sequences were carried out using the GCG Sequence Analysis Software Package (Madison, Wis.; pileup, peptide structure and motif programs), FASTA and BLAST search programs, and the PC/Gene software suite from Intelligenetics (San Francisco, Calif.; protein analysis programs). Northern blot analysis was conducted using total (20 μg/lane) or poly (A)+ mRNA (5–10 μg/lane) prepared as described above. RNA was fractionated on a 1% agarose gel containing 2.2M formaldehyde and blotted to a nitrocellulose membrane. Blots were hybridized with a PCR generated probe encompassing the majority of the ORF predicted by clone 7-3 (nt 291 to 1132). The probe was radiolabeled by random-priming with [α]$^{32}$P-dCTP to a specific activity of greater than 10$^9$ dpm/μg. Blots were pre-hybridized at 42° C. for 4 hrs. in 5×SSC, 5×Denhardt's solution, 250 μg/ml tRNA, 1% glycine, 0.075% SDS, 50 mM NaPO$_4$ (pH 6) and 50% formamide. Hybridizations were carried out at 42° C. for 20 hrs. in 5×SSC, 1×Denhardt's solution, 0.1% SDS, 50 mM NaPO$_4$, and 50% formamide. RNA blots were washed in 2×SSC, 0.2% SDS at 42° C. and at −70° C. RNA size markers were 28S and 18S rRNA and in vitro transcribed RNA markers (Novagen). Nylon membranes containing EcoR I and Hind III digested genomic DNA from several species (Clontech; 10 mg/lane) were hybridized for 24 hrs. at 30° C. in 6×SSPE, 10×Denhardt's, 1% SDS, and 50% formamide. Genomic blots were washed twice with room temperature 6×SSPE, twice with 55° C. 6×SSPE, and twice with 55° C. 4×SSPE. Additional swine GHSR clones from the swine cDNA library (described above) were identified by hybridization to plasmid DNA (in pools of 500 clones each) immobilized to nylon membranes in a slot-blot apparatus (Scheicher and Schuell). Pure clonal isolates were subsequently identified by colony hybridization. Swine GHSR clones that extend further in a 5' direction were identified using 5' RACE procedures (Frohman, M. A., 1993 *Methods Enzymol.* 218:340–358, which is incorporated by reference) using swine pituitary poly (A)+ mRNA as template.

EXAMPLE 10

Human GHSR

Human pituitary homologues of the swine GHSR were obtained by screening a commercially available cDNA library constructed in the vector lambda ZAP II (Stratagene) as per the manufacturer's instructions. Approximately 1.86× $10^6$ phages were initially plated and screened using a random-primer labeled portion of swine clone 7-3 (described above) as hybridization probe. Twenty one positive clones were plaque purified. The inserts from these clones were excised from the bacteriophage into the phagemid pBluescript II SK- by co-infection with helper phage as described by the manufacturer (Stratagene). Human clones were characterized as has been described above for the swine clone.

EXAMPLE 11

DNA Encoding a Rat Growth Hormone Secretagogue Receptor (GHSR) Type Ia

Cross-hybridization under reduced stringency was the strategy utilized to isolate the rat GHSR type Ia. Approximately $10^6$ phage plaques of a once-amplified rat pituitary cDNA library in lambda gt11 (RL 1051b; Clontech, Palo Alto, Calif.) were plated on *E. coli* strain Y1090r−. The plaques were transferred to maximum-strength Nytran (Schleicher & Schuell, Keene, N.H.) denatured, neutralized and screened with a 1.6 kb EcoRI/NotI fragment containing the entire coding and untranslated regions of the swine GHSR, clone 7-3. The membranes were incubated at 30° C. in prehybridization solution (50% formamide, 2 ×Denhardts, 5×SSPE, 0.1% SDS, 100 μg/ml salmon sperm DNA) for 3 hours followed by overnight incubation in hybridization solution (50% formamide, 2×Denhardts, 5×SSPE, 0.1% SDS, 10% dextran sulfate, 100 μg/ml salmon sperm DNA) with 1×10$^6$ cpm/ml of [$^{32}$P]-labeled probe. The probe was labeled with [$^{32}$P]dCTP using a random priming kit (Gibco BRL, Gaithersburg, Md.). After hybridization the blots were washed two times each with 2×SSC, 0.1% SDS (at 24° C., then 37° C., and finally 55° C.). A single positive clone was isolated following three rounds of plaque purification. Phage containing the GHSR was eluted from plate plaques with 1×lambda buffer (0.1M NaCl, 0.01M MgSO$_4$.7H$_2$O, 35mM Tris-HCl, pH 7.5) following overnight growth of approximately 200 pfu/150 mm dish. After a ten minute centrifugation at 10,000×/g to remove debris, the phage solution was treated with 1 μg/ml RNAse A and DNAse I for thirty minutes at 24° C., followed by precipitation with 20% PEG (8000)/2M NaCl for two hours on ice, and collection by centrifugation at 10,000×/g for twenty minutes. Phage DNA was isolated by incubation in 0.1% SDS, 30 mM EDTA, 50 μg/ml proteinase K for one hour at 68° C., with subsequent phenol (three times) and chloroform (twice) extraction before isopropanol precipitation overnight. The GHSR DNA insert (~6.4 kb) was sub-cloned from lambda gt1 I into the plasmid vector Litmus 28 (New England Biolabs, Beverly, Mass.). 2 μg of phage DNA was heated to 65° C. for ten minutes, then digested with 100 units BsiWI (New England Biolab, Beverly, Mass.) at 37° C. overnight. A 6.5 kb fragment was gel purified, electroeluted and phenol/chloroform extracted prior to ligation to BsiWI-digested Litmus 28 vector.

Double-stranded DNA was sequenced on both strands on a ABI 373 automated sequencer using the ABI PRISM dye termination cycle sequencing ready reaction kit (Perkin Elmer; Foster City, Calif.).

For sequence comparisons and functional expression studies, a contiguous DNA fragment encoding the complete ORF (devoid of intervening sequence) for the rat GHSR type Ia was generated. The PCR was utilized to synthesize a amino-terminal fragment from Met-1 to Val-260 with EcoRI (5') and HpaI (3') restriction sites appended, while a carboxyl-terminal fragment was generated from Lys-261 to Thr-364 with Dra I (5') and Not I (3') restriction sites appended. The ORF construct was assembled into the mammalian expression vector pSV7 via a three-way ligation with EcoRI/Not I-digested pSV7, EcoRI/Hpa I-digested NH$_2$-terminal fragment, and Dra I/Not I-digested C-terminal fragment.

Functional activity of the ORF construct was assessed by transfecting (using lipofectamine; GIBCO/BRL) 5 μg of plasmid DNA into the aequorin expressing reporter cell line (293-AEQ17) cultured in 60 mm dishes. Following approximately 40 hours of expression the aequorin in the cells was charged for 2 hours with coelenterazine, the cells were harvested, washed and pelleted by low speed centrifugation into luminometer tubes. Functional activity was determined by measuring Compound A dependent mobilization of intracellular calcium and concomitant calcium induced aequorin bioluminescence. Shown in FIG. 26 are three replicate samples exhibiting Compound A induced luminescent responses.

EXAMPLE 12

Assays

Mammalian cells (COS-7) were transfected with GHSR expression plasmids using Lipofectamine (GIBCO-BRL; Hawley-Nelson, 1993, *Focus* 15:73). Transfections were performed in 60 mm dishes on 80% confluent cells (approximately 4×10$^5$ cells) with 8 μg of Lipofectamine and 32 μg of GHSR plasmid DNA.

Binding of [$^{35}$S]-Compound A to swine pituitary membranes and crude membranes prepared from COS-7 cells transfected with GHSR expression plasmids was conducted. Crude cell membranes from COS-7 transfectants were prepared on ice, 48 hrs. post-transfection. Each 60 mm dish was washed twice with 3 ml of PBS, once with 1 ml homogenization buffer (50 mM Tris-HCl [pH 7.4], 5 mM MgCl$_2$, 2.5 mM EDTA, 30 μg/ml bacitracin). 0.5 ml of homogenization buffer was added to each dish, cells were removed by scraping and then homogenized using a Polytron device (Brinkmann, Syosset, N.Y.; 3 bursts of 10 sec. at setting 4).

The homogenate was then centrifuged for 20 min. at 11,000×g at 0° C. and the resulting crude membrane pellet (chiefly containing cell membranes and nuclei) was resuspended in homogenization buffer supplemented with 0.06% BSA (0.1 ml/60 mm dish) and kept on ice. Binding reactions were performed at 20° C. for 1 hr. in a total volume of 0.5 ml containing: 0.1 ml of membrane suspension, 10 µl of [$^{35}$S]-Compound A (0.05 to 1 nM; specific activity approximately 900 Ci/mmol), 10 µl of competing drug and 380–390 µl of homogenization buffer. Bound radioligand was separated by rapid vacuum filtration (Brandel 48-well cell harvester) through GF/C filters pretreated for 1 hr. with 0.5% polyethylenimine. After application of the membrane suspension to the filter, the filters were washed 3 times with 3 ml each of ice cold 50 mM Tris-HCl [pH 7.4], 10 mM $MgCl_2$, 2.5 mM EDTA and 0.015% Triton X-100, and the bound radioactivity on the filers was quantitated by scintillation counting. Specific binding (>90% of total) is defined as the difference between total binding and non-specific binding conducted in the presence of 50 nM unlabeled Compound A.

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 1063 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
CCTCACGCTG CCAGACCTGG GCTGGGACGC TCCCCCTGAA AACGACTCGC TAGTGGAGGA      60

GCTGCTGCCG CTCTTCCCCA CGCCGCTGTT GGCGGGCGTC ACCGCCACCT GCGTGGCGCT     120

CTTCGTGGTG GGTATCGCGG GCAACCTGCT CACGATGCTG GTAGTGTCAC GCTTCCGCGA     180

GATGCGCACC ACCACCAACC TCTACCTGTC CAGCATGGCC TTCTCCGACC TACTCATCTT     240

CCTCTGCATG CCCCTCGACC TCTTCCGCCT CTGGCAGTAC CGGCCTTGGA ACCTTGGCAA     300

CCTGCTCTGC AAACTCTTCC AGTTCGTTAG CGAGAGCTGC ACCTACGCCA CAGTGCTCAC     360

CATCACCGCG CTGAGCGTCG AGCGCTACTT CGCCATCTGC TTCCCGCTGC GGGCCAAGGT     420

AGTGGTCACC AAGGGCCGGG TAAAGCTGGT CATCCTGGTC ATCTGGGCCG TGGCCTTCTG     480

CAGCGCCGGG CCCATCTTCG TGCTGGTCGG AGTGGAGCAT GATAACGGCA CTGACCCTCG     540

GGACACCAAC GAGTGCCGCG CCACGGAGTT CGCCGTGCGC TCCGGGCTGC TTACCGTCAT     600

GGTCTGGGTG TCCAGTGTCT TCTTCTTCCT GCCTGTCTTC TGCCTCACTG TGCTCTATAG     660

CCTCATCGGC AGGAAGCTCT GGCGGAGGAA GCGCGGCGAG GCGGCGGTGG GCTCCTCGCT     720

CAGGGACCAG AACCACAAAC AAACCGTGAA AATGCTGGCT GTAGTGGTGT TTGCTTTCAT     780

ACTCTGCTGG CTGCCTTTCC ATGTAGGGCG ATATTTATTT TCCAAATCCT GGAGCCTGG      840

CTCTGTGGAG ATTGCTCAGA TCAGCCAATA CTGCAACCTC GTGTCCTTTG TCCTCTTCTA     900

CCTCAGTGCG GCCATCAACC CTATTCTGTA CAACATCATG TCCAAGAAGT ATCGGGTGGC     960

GGTGTTCAAA CTGCTGGGAT TGAGCCCTT CTCACAGAGG AAACTCTCCA CTCTGAAGGA    1020

TGAAAGTTCT CGGGCCTGGA CAGAATCTAG TATTAATACA TGA                     1063
```

(2) INFORMATION FOR SEQ ID NO: 2:

(i) SEQUENCE CHARACTERISTICS:
      (A) LENGTH: 302 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

Met Leu Val Val Ser Arg Phe Arg Glu Met Arg Thr Thr Thr Asn Leu
 1               5                   10                  15

Tyr Leu Ser Ser Met Ala Phe Ser Asp Leu Leu Ile Phe Leu Cys Met
                20                  25                  30

Pro Leu Asp Leu Phe Arg Leu Trp Gln Tyr Arg Pro Trp Asn Leu Gly
            35                  40                  45

Asn Leu Leu Cys Lys Leu Phe Gln Phe Val Ser Glu Ser Cys Thr Tyr
        50                  55                  60

Ala Thr Val Leu Thr Ile Thr Ala Leu Ser Val Glu Arg Tyr Phe Ala
65                  70                  75                  80

Ile Cys Phe Pro Leu Arg Ala Lys Val Val Thr Lys Gly Arg Val
                85                  90                  95

Lys Leu Val Ile Leu Val Ile Trp Ala Val Ala Phe Cys Ser Ala Gly
                100                 105                 110

Pro Ile Phe Val Leu Val Gly Val Glu His Asp Asn Gly Thr Asp Pro
                115                 120                 125

Arg Asp Thr Asn Glu Cys Arg Ala Thr Glu Phe Ala Val Arg Ser Gly
        130                 135                 140

Leu Leu Thr Val Met Val Trp Val Ser Ser Val Phe Phe Leu Pro
145                 150                 155                 160

Val Phe Cys Leu Thr Val Leu Tyr Ser Leu Ile Gly Arg Lys Leu Trp
                165                 170                 175

Arg Arg Lys Arg Gly Glu Ala Ala Val Gly Ser Ser Leu Arg Asp Gln
                180                 185                 190

Asn His Lys Gln Thr Val Lys Met Leu Ala Val Val Phe Ala Phe
        195                 200                 205

Ile Leu Cys Trp Leu Pro Phe His Val Gly Arg Tyr Leu Phe Ser Lys
        210                 215                 220

Ser Leu Glu Pro Gly Ser Val Glu Ile Ala Gln Ile Ser Gln Tyr Cys
225                 230                 235                 240

Asn Leu Val Ser Phe Val Leu Phe Tyr Leu Ser Ala Ala Ile Asn Pro
                245                 250                 255

Ile Leu Tyr Asn Ile Met Ser Lys Lys Tyr Arg Val Ala Val Phe Lys
                260                 265                 270

Leu Leu Gly Phe Glu Pro Phe Ser Gln Arg Lys Leu Ser Thr Leu Lys
            275                 280                 285

Asp Glu Ser Ser Arg Ala Trp Thr Glu Ser Ser Ile Asn Thr
290                 295                 300

(2) INFORMATION FOR SEQ ID NO: 3:

(i) SEQUENCE CHARACTERISTICS:
        (A) LENGTH: 353 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Leu Thr Leu Pro Asp Leu Gly Trp Asp Ala Pro Pro Glu Asn Asp Ser
 1               5                   10                  15

Leu Val Glu Glu Leu Leu Pro Leu Phe Pro Thr Pro Leu Leu Ala Gly

```
            20                  25                  30
Val Thr Ala Thr Cys Val Ala Leu Phe Val Val Gly Ile Ala Gly Asn
            35                  40                  45

Leu Leu Thr Met Leu Val Val Ser Arg Phe Arg Glu Met Arg Thr Thr
 50                  55                  60

Thr Asn Leu Tyr Leu Ser Ser Met Ala Phe Ser Asp Leu Leu Ile Phe
 65                  70                  75                  80

Leu Cys Met Pro Leu Asp Leu Phe Arg Leu Trp Gln Tyr Arg Pro Trp
                 85                  90                  95

Asn Leu Gly Asn Leu Leu Cys Lys Leu Phe Gln Phe Val Ser Glu Ser
                100                 105                 110

Cys Thr Tyr Ala Thr Val Leu Thr Ile Thr Ala Leu Ser Val Glu Arg
                115                 120                 125

Tyr Phe Ala Ile Cys Phe Pro Leu Arg Ala Lys Val Val Thr Lys
                130                 135                 140

Gly Arg Val Lys Leu Val Ile Leu Val Ile Trp Ala Val Ala Phe Cys
145                 150                 155                 160

Ser Ala Gly Pro Ile Phe Val Leu Val Gly Val Glu His Asp Asn Gly
                165                 170                 175

Thr Asp Pro Arg Asp Thr Asn Glu Cys Arg Ala Thr Glu Phe Ala Val
                180                 185                 190

Arg Ser Gly Leu Leu Thr Val Met Val Trp Val Ser Ser Val Phe Phe
                195                 200                 205

Phe Leu Pro Val Phe Cys Leu Thr Val Leu Tyr Ser Leu Ile Gly Arg
                210                 215                 220

Lys Leu Trp Arg Lys Arg Gly Glu Ala Ala Val Gly Ser Ser Leu
225                 230                 235                 240

Arg Asp Gln Asn His Lys Gln Thr Val Lys Met Leu Ala Val Val Val
                245                 250                 255

Phe Ala Phe Ile Leu Cys Trp Leu Pro Phe His Val Gly Arg Tyr Leu
                260                 265                 270

Phe Ser Lys Ser Leu Glu Pro Gly Ser Val Glu Ile Ala Gln Ile Ser
                275                 280                 285

Gln Tyr Cys Asn Leu Val Ser Phe Val Leu Phe Tyr Leu Ser Ala Ala
290                 295                 300

Ile Asn Pro Ile Leu Tyr Asn Ile Met Ser Lys Lys Tyr Arg Val Ala
305                 310                 315                 320

Val Phe Lys Leu Leu Gly Phe Glu Pro Phe Ser Gln Arg Lys Leu Ser
                325                 330                 335

Thr Leu Lys Asp Glu Ser Ser Arg Ala Trp Thr Glu Ser Ser Ile
                340                 345                 350

Asn Thr (2) INFORMATION FOR SEQ ID NO: 4:

(i) SEQUENCE CHARACTERISTICS:
        (A) LENGTH: 1029 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GCAGCCTCTC ACTTCCCTCT TTCCTCTCCT AGCATCCTCC CTGAGAGCCC GCGCTCGATA         60
```

-continued

```
CTCCTTTGCA CTCTTTCGCG CCTAAGAGAA CCTTCTCTGG GACCAGCCGG CTCCACCCTC      120

TCGGTCCTAT CCAAGAGCCA GTTAAGCAGA GCCCTAAGCA TGTGGAACGC GACCCCGAGC      180

GAGGAACCGG GGCCCAACCT CACGCTGCCA GACCTGGGCT GGGACGCTCC CCCTGAAAAC      240

GACTCGCTAG TGGAGGAGCT GCTGCCGCTC TTCCCCACGC CGCTGTTGGC GGGCGTCACC      300

GCCACCTGCG TGGCGCTCTT CGTGGTGGGT ATCGCGGGCA ACCTGCTCAC GATGCTGGTA      360

GTGTCACGCT TCCGCGAGAT GCGCACCACC ACCAACCTCT ACCTGTCCAG CATGGCCTTC      420

TCCGAACTAC TCATCTTCCT CTGCATGCCC CTCGAACTCT TCCGCCTTTG GCAGTACCGG      480

CCTTGGAACC TTGGCAACCT GCTCTGCAAA CTCTTCCAGT TCGTTAGCGA GAGCTGCACC      540

TACGCCACAG TGCTCACCAT CACCGCGCTG AGCGTCGAGC GCTACTTCGC CATCTGCTTC      600

CCGCTGCGGG CCAAGGTAGT GGTCACCAAG GGCCGGGTAA AGCTGGTCAT CCTGGTCATC      660

TGGGCCGTGG CCTTCTGCAG CGCCGGGCCC ATCTTCGTGC TGGTCGGAGT GGAGCATGAT      720

AACGGCACTG ACCCTCGGGA CACCAACGAG TGCCGCGCCA CGGAGTTCGC CGTGCGCTCC      780

GGGCTGCTTA CCGTCATGGT CTGGGTGTCC AGTGTCTTCT TCTTCCTGCC TGTCTTCTGC      840

CTCACTGTGC TCTATAGCCT CATCGGCAGG AAGCTCTGGC GGAGGAAGCG CGGCGAGGCG      900

GCGGTGGGCT CCTCGCTCAG GGACCAGAAC CACAAACAAA CCGTGAAAAT GCTGGGTGGG      960

TCTCAATGCG CCCTCGAGCT TTCTCTCCCG GGTCCCCTCC ACTCCTCGTG CCTTTTCTCT     1020

TCTCCCTGA                                                            1029
```

(2) INFORMATION FOR SEQ ID NO: 5:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Trp Asn Ala Thr Pro Ser Glu Glu Pro Gly Pro Asn Leu Thr Leu
 1               5                  10                  15

Pro Asp Leu Gly Trp Asp Ala Pro Pro Glu Asn Asp Ser Leu Val Glu
            20                  25                  30

Glu Leu Leu Pro Leu Phe Pro Thr Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Met Arg Thr Thr Thr Asn Leu
65                  70                  75                  80

Tyr Leu Ser Ser Met Ala Phe Ser Glu Leu Leu Ile Phe Leu Cys Met
                85                  90                  95

Pro Leu Glu Leu Phe Arg Leu Trp Gln Tyr Arg Pro Trp Asn Leu Gly
            100                 105                 110

Asn Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Leu Val Ile Trp Ala Val Ala Phe Cys Ser Ala Gly
                165                 170                 175
```

```
Pro Ile Phe Val Leu Val Gly Val Glu His Asp Asn Gly Thr Asp Pro
            180                 185                 190

Arg Asp Thr Asn Glu Cys Arg Ala Thr Glu Phe Ala Val Arg Ser Gly
            195                 200                 205

Leu Leu Thr Val Met Val Trp Val Ser Ser Val Phe Phe Leu Pro
            210                 215                 220

Val Phe Cys Leu Thr Val Leu Tyr Ser Leu Ile Gly Arg Lys Leu Trp
225                 230                 235                 240

Arg Arg Lys Arg Gly Glu Ala Ala Val Gly Ser Ser Leu Arg Asp Gln
            245                 250                 255

Asn His Lys Gln Thr Val Lys Met Leu Gly Gly Ser Gln Cys Ala Leu
            260                 265                 270

Glu Leu Ser Leu Pro Gly Pro Leu His Ser Ser Cys Leu Phe Ser Ser
            275                 280                 285

Pro
```

(2) INFORMATION FOR SEQ ID NO: 6:

(i) SEQUENCE CHARACTERISTICS:
        (A) LENGTH: 1088 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
CGCCCAGCGA AGAGCCGGGG TTCAACCTCA CACTGGCCGA CCTGGACTGG GATGCTTCCC     60
CCGGCAACGA CTCGCTGGGC GACGAGCTGC TGCAGCTCTT CCCCGCGCCG CTGCTGGCGG    120
GCGTCACAGC CACCTGCGTG GCACTCTTCG TGGTGGGTAT CGCTGGCAAC CTGCTCACCA    180
TGCTGGTGGT GTCGCGCTTC CGCGAGCTGC GCACCACCAC CAACCTCTAC CTGTCCAGCA    240
TGGCCTTCTC CGATCTGCTC ATCTTCCTCT GCATGCCCCT GGACCTCGTT CGCCTCTGGC    300
AGTACCGGCC CTGGAACTTC GGCGACCTCC TCTGCAAACT CTTCCAATTC GTCAGTGAGA    360
GCTGCACCTA CGCCACGGTG CTCACCATCA CAGCGCTGAG CGTCGAGCGC TACTTCGCCA    420
TCTGCTTCCC ACTCCGGGCC AAGGTGGTGG TCACCAAGGG GCGGGTGAAG CTGGTCATCT    480
TCGTCATCTG GGCCGTGGCC TTCTGCAGCG CCGGGCCCAT CTTCGTGCTA GTCGGGGTGG    540
AGCACGAGAA CGGCACCGAC CCTTGGGACA CCAACGAGTG CCGCCCCACC GAGTTTGCGG    600
TGCGCTCTGG ACTGCTCACG GTCATGGTGT GGGTGTCCAG CATCTTCTTC TTCCTTCCTG    660
TCTTCTGTCT CACGGTCCTC TACAGTCTCA TCGGCAGGAA GCTGTGGCGG AGGAGGCGCG    720
GCGATGCTGT CGTGGGTGCC TCGCTCAGGG ACCAGAACCA CAAGCAAACC GTGAAAATGC    780
TGGCTGTAGT GGTGTTTGCC TTCATCCTCT GCTGGCTCCC CTTCCACGTA GGGCGATATT    840
TATTTTCCAA ATCCTTTGAG CCTGGCTCCT TGGAGATTGC TCAGATCAGC CAGTACTGCA    900
ACCTCGTGTC CTTTGTCCTC TTCTACCTCA GTGCTGCCAT CAACCCCATT CTGTACAACA    960
TCATGTCCAA GAAGTACCGG GTGGCAGTGT TCAGACTTCT GGGATTCGAA CCCTTCTCCC   1020
AGAGAAAGCT CTCCACTCTG AAAGATGAAA GTTCTCGGGC CTGGACAGAA TCTAGTATTA   1080
ATACATGA                                                           1088
```

(2) INFORMATION FOR SEQ ID NO: 7:

(i) SEQUENCE CHARACTERISTICS:

(A) LENGTH: 302 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 7:

```
Met Leu Val Val Ser Arg Phe Arg Glu Leu Arg Thr Thr Thr Asn Leu
 1               5                  10                  15

Tyr Leu Ser Ser Met Ala Phe Ser Asp Leu Leu Ile Phe Leu Cys Met
                20                  25                  30

Pro Leu Asp Leu Val Arg Leu Trp Gln Tyr Arg Pro Trp Asn Phe Gly
            35                  40                  45

Asp Leu Leu Cys Lys Leu Phe Gln Phe Val Ser Glu Ser Cys Thr Tyr
 50                  55                  60

Ala Thr Val Leu Thr Ile Thr Ala Leu Ser Val Glu Arg Tyr Phe Ala
 65                  70                  75                  80

Ile Cys Phe Pro Leu Arg Ala Lys Val Val Thr Lys Gly Arg Val
                85                  90                  95

Lys Leu Val Ile Phe Val Ile Trp Ala Val Ala Phe Cys Ser Ala Gly
                100                 105                 110

Pro Ile Phe Val Leu Val Gly Val Glu His Glu Asn Gly Thr Asp Pro
            115                 120                 125

Trp Asp Thr Asn Glu Cys Arg Pro Thr Glu Phe Ala Val Arg Ser Gly
    130                 135                 140

Leu Leu Thr Val Met Val Trp Val Ser Ser Ile Phe Phe Leu Pro
145                 150                 155                 160

Val Phe Cys Leu Thr Val Leu Tyr Ser Leu Ile Gly Arg Lys Leu Trp
                165                 170                 175

Arg Arg Arg Arg Gly Asp Ala Val Val Gly Ala Ser Leu Arg Asp Gln
                180                 185                 190

Asn His Lys Gln Thr Val Lys Met Leu Ala Val Val Phe Ala Phe
                195                 200                 205

Ile Leu Cys Trp Leu Pro Phe His Val Gly Arg Tyr Leu Phe Ser Lys
    210                 215                 220

Ser Phe Glu Pro Gly Ser Leu Glu Ile Ala Gln Ile Ser Gln Tyr Cys
225                 230                 235                 240

Asn Leu Val Ser Phe Val Leu Phe Tyr Leu Ser Ala Ala Ile Asn Pro
                245                 250                 255

Ile Leu Tyr Asn Ile Met Ser Lys Lys Tyr Arg Val Ala Val Phe Arg
                260                 265                 270

Leu Leu Gly Phe Glu Pro Phe Ser Gln Arg Lys Leu Ser Thr Leu Lys
                275                 280                 285

Asp Glu Ser Ser Arg Ala Trp Thr Glu Ser Ser Ile Asn Thr
290                 295                 300
```

(2) INFORMATION FOR SEQ ID NO: 8:

(i) SEQUENCE CHARACTERISTICS:
(A) LENGTH: 361 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 8:

```
Pro Ser Glu Glu Pro Gly Phe Asn Leu Thr Leu Ala Asp Leu Asp Trp
1               5                   10                  15

Asp Ala Ser Pro Gly Asn Asp Ser Leu Gly Asp Glu Leu Leu Gln Leu
            20                  25                  30

Phe Pro Ala Pro Leu Leu Ala Gly Val Thr Ala Thr Cys Val Ala Leu
        35                  40                  45

Phe Val Val Gly Ile Ala Gly Asn Leu Leu Thr Met Leu Val Val Ser
    50                  55                  60

Arg Phe Arg Glu Leu Arg Thr Thr Thr Asn Leu Tyr Leu Ser Ser Met
65              70                  75                  80

Ala Phe Ser Asp Leu Leu Ile Phe Leu Cys Met Pro Leu Asp Leu Val
                85                  90                  95

Arg Leu Trp Gln Tyr Arg Pro Trp Asn Phe Gly Asp Leu Leu Cys Lys
            100                 105                 110

Leu Phe Gln Phe Val Ser Glu Ser Cys Thr Tyr Ala Thr Val Leu Thr
            115                 120                 125

Ile Thr Ala Leu Ser Val Glu Arg Tyr Phe Ala Ile Cys Phe Pro Leu
    130                 135                 140

Arg Ala Lys Val Val Thr Lys Gly Arg Val Lys Leu Val Ile Phe
145             150                 155                 160

Val Ile Trp Ala Val Ala Phe Cys Ser Ala Gly Pro Ile Phe Val Leu
            165                 170                 175

Val Gly Val Glu His Glu Asn Gly Thr Asp Pro Trp Asp Thr Asn Glu
            180                 185                 190

Cys Arg Pro Thr Glu Phe Ala Val Arg Ser Gly Leu Leu Thr Val Met
        195                 200                 205

Val Trp Val Ser Ser Ile Phe Phe Leu Pro Val Phe Cys Leu Thr
    210                 215                 220

Val Leu Tyr Ser Leu Ile Gly Arg Lys Leu Trp Arg Arg Arg Gly
225             230                 235                 240

Asp Ala Val Val Gly Ala Ser Leu Arg Asp Gln Asn His Lys Gln Thr
            245                 250                 255

Val Lys Met Leu Ala Val Val Phe Ala Phe Ile Leu Cys Trp Leu
        260                 265                 270

Pro Phe His Val Gly Arg Tyr Leu Phe Ser Lys Ser Phe Glu Pro Gly
        275                 280                 285

Ser Leu Glu Ile Ala Gln Ile Ser Gln Tyr Cys Asn Leu Val Ser Phe
    290                 295                 300

Val Leu Phe Tyr Leu Ser Ala Ala Ile Asn Pro Ile Leu Tyr Asn Ile
305                 310                 315                 320

Met Ser Lys Lys Tyr Arg Val Ala Val Phe Arg Leu Leu Gly Phe Glu
            325                 330                 335

Pro Phe Ser Gln Arg Lys Leu Ser Thr Leu Lys Asp Glu Ser Ser Arg
            340                 345                 350

Ala Trp Thr Glu Ser Ser Ile Asn Thr
            355                 360

(2) INFORMATION FOR SEQ ID NO: 9:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 9:

```
GCGCCTCACG CTCCCGCTTC GCGGCGCCTG GTCCCTGCGG TCCCCACTCG CTGCGACGCT      60

TTGGGAAGTG CGAGATGGAA CTGGATCGAG AACGCAAATG CGAGGCAGGG CTGGTGACAG     120

CATCCTCCCT ACGCGTCTGC ACCCGCTCCT CCCTCGCACC CTCCCGCGCC TAAGCGGACC     180

TCCTCGGGAG CCAGCTCGGT CCAGCCTCCC AGCGCAGTCA CGTCCCAGAG CCTGTTCAGC     240

TGAGCCGGCA GCATGTGGAA CGCGACGCCC AGCGAAGAGC CGGGGTTCAA CCTCACACTG     300

GCCGACCTGG ACTGGGATGC TTCCCCCGGC AACGACTCGC TGGGCGACGA GCTGCTGCAG     360

CTCTTCCCCG CGCCGCTGCT GGCGGGCGTC ACAGCCACCT GCGTGGCACT CTTCGTGGTG     420

GGTATCGCTG GCAACCTGCT CACCATGCTG GTGGTGTCGC GCTTCCGCGA GCTGCGCACC     480

ACCACCAACC TCTACCTGTC CAGCATGGCC TTCTCCGATC TGCTCATCTT CCTCTGCATG     540

CCCCTGGACC TCGTTCGCCT CTGGCAGTAC CGGCCCTGGA ACTTCGGCGA CCTCCTCTGC     600

AAACTCTTCC AATTCGTCAG TGAGAGCTGC ACCTACGCCA CGGTGCTCAC CATCACAGCG     660

CTGAGCGTCG AGCGCTACTT CGCCATCTGC TTCCCACTCC GGGCCAAGGT GGTGGTCACC     720

AAGGGGCGGG TGAAGCTGGT CATCTTCGTC ATCTGGGCCG TGGCCTTCTG CAGCGCCGGG     780

CCCATCTTCG TGCTAGTCGG GGTGGAGCAC GAGAACGGCA CCGACCCTTG GGACACCAAC     840

GAGTGCCGCC CCACCGAGTT TGCGGTGCGC TCTGGACTGC TCACGGTCAT GGTGTGGGTG     900

TCCAGCATCT TCTTCTTCCT TCCTGTCTTC TGTCTCACGG TCCTCTACAG TCTCATCGGC     960

AGGAAGCTGT GGCGGAGGAG GCGCGGCGAT GCTGTCGTGG GTGCCTCGCT CAGGGACCAG    1020

AACCACAAGC AAACCGTGAA AATGCTGGGT GGGTCTCAGC GCGCGCTCAG GCTTTCTCTC    1080

GCGGGTCCTA TCCTCTCCCT GTGCCTTCTC CCTTCTCTCT GA                       1122
```

(2) INFORMATION FOR SEQ ID NO: 10:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Met Trp Asn Ala Thr Pro Ser Glu Glu Pro Gly Phe Asn Leu Thr Leu
 1               5                  10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
```

```
              130                 135                 140
Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
                180                 185                 190

Trp Asp Thr Asn Glu Cys Arg Pro Thr Glu Phe Ala Val Arg Ser Gly
            195                 200                 205

Leu Leu Thr Val Met Val Trp Val Ser Ser Ile Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Gly Gly Ser Gln Arg Ala Leu
                260                 265                 270

Arg Leu Ser Leu Ala Gly Pro Ile Leu Ser Leu Cys Leu Leu Pro Ser
        275                 280                 285

Leu (2) INFORMATION FOR SEQ ID NO: 11:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

ATCTGCTCAT CTTCCTCTGC ATGCCCCTGG ACCTCGTTCG CCTCTGGCAG TACCGGCCCT      60

GGAACTTCGG CGACCTCCTC TGCAAACTCT TCCAATTCGT CAGTGAGAGC TGCACCTACG     120

CCACGGTGCT CACCATCACA GCGCTGAGCG TCGAGCGCTA CTTCGCCATC TGCTTCCCAC     180

TCCGGGCCAA GGTGGTGGTC ACCAAGGGGC GGGTGAAGCT GGTCATCTTC GTCATCTGGG     240

CCGTGGCCTT CTGCAGCGCC GGGCCCATCT TCGTGCTAGT CGGGGTGGAG CACGAGAACG     300

GCACCGACCC TTGGGACACC AACGAGTGCC GCCCCACCGA GTTTGCGGTG CGCTCTGGAC     360

TGCTCACGGT CATGGTGTGG GTGTCCAGCA TCTTCTTCTT CCTTCCTGTC TTCTGTCTCA     420

CGGTCCTCTA CAGTCTCATC GGCAGGAAGC TGTGGCGGAG GAGGCGCGGC GATGCTGTCG     480

TGGGTGCCTC GCTCAGGGAC CAGAACCACA AGCAAACCGT GAAAATGCTG GCTGTAGTGG     540

TGTTTGCCTT CATCCTCTGC TGGCTCCCCT TCCACGTAGG GCGATATTTA TTTTCCAAAT     600

CCTTTGAGCC TGGCTCCTTG GAGATTGCTC AGATCAGCCA GTACTGCAAC CTCGTGTCCT     660

TTGTCCTCTT CTACCTCAGT GCTGCCATCA ACCCCATTCT GTACAACATC ATGTCCAAGA     720

AGTACCGGGT GGCAGTGTTC AGACTTCTGG GATTCGAACC CTTCTCCCAG AGAAAGCTCT     780

CCACTCTGAA AGATGAAAGT TCTCGGGCCT GGACAGAATC TAGTATTAAT ACATGA         836

(2) INFORMATION FOR SEQ ID NO: 12:

(i) SEQUENCE CHARACTERISTICS:
        (A) LENGTH: 271 amino acids
        (B) TYPE: amino acid
        (C) STRANDEDNESS: single
```

```
         (D) TOPOLOGY: linear (ii) MOLECULE TYPE: protein (xi) SEQUENCE DESCRIPTION: SEQ ID NO: 12:

Met Pro Leu Asp Leu Val Arg Leu Trp Gln Tyr Arg Pro Trp Asn Phe
  1               5                  10                  15

Gly Asp Leu Leu Cys Lys Leu Phe Gln Phe Val Ser Glu Ser Cys Thr
             20                  25                  30

Tyr Ala Thr Val Leu Thr Ile Thr Ala Leu Ser Val Glu Arg Tyr Phe
             35                  40                  45

Ala Ile Cys Phe Pro Leu Arg Ala Lys Val Val Thr Lys Gly Arg
 50                  55                  60

Val Lys Leu Val Ile Phe Val Ile Trp Ala Val Ala Phe Cys Ser Ala
 65                  70                  75                  80

Gly Pro Ile Phe Val Leu Val Gly Val Glu His Glu Asn Gly Thr Asp
             85                  90                  95

Pro Trp Asp Thr Asn Glu Cys Arg Pro Thr Glu Phe Ala Val Arg Ser
            100                 105                 110

Gly Leu Leu Thr Val Met Val Trp Val Ser Ser Ile Phe Phe Phe Leu
            115                 120                 125

Pro Val Phe Cys Leu Thr Val Leu Tyr Ser Leu Ile Gly Arg Lys Leu
            130                 135                 140

Trp Arg Arg Arg Arg Gly Asp Ala Val Val Gly Ala Ser Leu Arg Asp
145                 150                 155                 160

Gln Asn His Lys Gln Thr Val Lys Met Leu Ala Val Val Phe Ala
            165                 170                 175

Phe Ile Leu Cys Trp Leu Pro Phe His Val Gly Arg Tyr Leu Phe Ser
            180                 185                 190

Lys Ser Phe Glu Pro Gly Ser Leu Glu Ile Ala Gln Ile Ser Gln Tyr
            195                 200                 205

Cys Asn Leu Val Ser Phe Val Leu Phe Tyr Leu Ser Ala Ala Ile Asn
            210                 215                 220

Pro Ile Leu Tyr Asn Ile Met Ser Lys Lys Tyr Arg Val Ala Val Phe
225                 230                 235                 240

Arg Leu Leu Gly Phe Glu Pro Phe Ser Gln Arg Lys Leu Ser Thr Leu
            245                 250                 255

Lys Asp Glu Ser Ser Arg Ala Trp Thr Glu Ser Ser Ile Asn Thr
            260                 265                 270

(2) INFORMATION FOR SEQ ID NO: 13:

(i) SEQUENCE CHARACTERISTICS:
        (A) LENGTH: 366 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Met Trp Asn Ala Thr Pro Ser Glu Glu Pro Gly Phe Asn Leu Thr Leu
  1               5                  10                  15

Ala Asp Leu Asp Trp Asp Ala Ser Pro Gly Asn Asp Ser Leu Gly Asp
             20                  25                  30

Glu Leu Leu Gln Leu Phe Pro Ala Pro Leu Leu Ala Gly Val Thr Ala
             35                  40                  45
```

```
Thr Cys Val Ala Leu Phe Val Val Gly Ile Ala Gly Asn Leu Leu Thr
         50                  55                  60
Met Leu Val Val Ser Arg Phe Arg Glu Leu Arg Thr Thr Thr Asn Leu
 65                  70                  75                  80
Tyr Leu Ser Ser Met Ala Phe Ser Asp Leu Leu Ile Phe Leu Cys Met
                 85                  90                  95
Pro Leu Asp Leu Val Arg Leu Trp Gln Tyr Arg Pro Trp Asn Phe Gly
            100                 105                 110
Asp Leu Leu Cys Lys Leu Phe Gln Phe Val Ser Glu Ser Cys Thr Tyr
            115                 120                 125
Ala Thr Val Leu Thr Ile Thr Ala Leu Ser Val Glu Arg Tyr Phe Ala
    130                 135                 140
Ile Cys Phe Pro Leu Arg Ala Lys Val Val Thr Lys Gly Arg Val
145                 150                 155                 160
Lys Leu Val Ile Phe Val Ile Trp Ala Val Ala Phe Cys Ser Ala Gly
                165                 170                 175
Pro Ile Phe Val Leu Val Gly Val Glu His Glu Asn Gly Thr Asp Pro
            180                 185                 190
Trp Asp Thr Asn Glu Cys Arg Pro Thr Glu Phe Ala Val Arg Ser Gly
        195                 200                 205
Leu Leu Thr Val Met Val Trp Val Ser Ser Ile Phe Phe Phe Leu Pro
    210                 215                 220
Val Phe Cys Leu Thr Val Leu Tyr Ser Leu Ile Gly Arg Lys Leu Trp
225                 230                 235                 240
Arg Arg Arg Arg Gly Asp Ala Val Val Gly Ala Ser Leu Arg Asp Gln
                245                 250                 255
Asn His Lys Gln Thr Val Lys Met Leu Ala Val Val Val Phe Ala Phe
            260                 265                 270
Ile Leu Cys Trp Leu Pro Phe His Val Gly Arg Tyr Leu Phe Ser Lys
        275                 280                 285
Ser Phe Glu Pro Gly Ser Leu Glu Ile Ala Gln Ile Ser Gln Tyr Cys
    290                 295                 300
Asn Leu Val Ser Phe Val Leu Phe Tyr Leu Ser Ala Ala Ile Asn Pro
305                 310                 315                 320
Ile Leu Tyr Asn Ile Met Ser Lys Lys Tyr Arg Val Ala Val Phe Arg
                325                 330                 335
Leu Leu Gly Phe Glu Pro Phe Ser Gln Arg Lys Leu Ser Thr Leu Lys
            340                 345                 350
Asp Glu Ser Ser Arg Ala Trp Thr Glu Ser Ser Ile Asn Thr
        355                 360                 365
```

(2) INFORMATION FOR SEQ ID NO: 14:

(i) SEQUENCE CHARACTERISTICS:
        (A) LENGTH: 3129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
ATGTGGAACG CGACCCCCAG CGAGGAGCCG GAGCCTAACG TCACGTTGGA CCTGGATTGG    60
GACGCTTCCC CCGGCAACGA CTCACTGCCT GACGAACTGC TGCCGCTGTT CCCCGCTCCG   120
CTGCTGGCAG GCGTCACCGC CACCTGCGTG GCGCTCTTCG TGGTGGGCAT CTCAGGCAAC   180
```

```
CTGCTCACTA TGCTGGTGGT GTCCCGCTTC CGCGAGCTGC GCACCACCAC CAACCTCTAC    240

CTGTCCAGCA TGGCCTTCTC GGATCTGCTC ATCTTCCTGT GCATGCCGCT GGACCTCGTC    300

CGCCTCTGGC AGTACCGGCC CTGGAACTTC GGCGACCTGC TCTGCAAACT CTTCCAGTTT    360

GTCAGCGAGA GCTGCACCTA CGCCACGGTC CTCACCATCA CCGCGCTGAG CGTCGAGCGC    420

TACTTCGCCA TCTGCTTCCC TCTGCGGGCC AAGGTGGTGG TCACTAAGGG CCGCGTGAAG    480

CTGGTCATCC TTGTCATCTG GGCCGTGGCT TTCTGCAGCG CGGGGCCCAT CTTCGTGCTG    540

GTGGGCGTGG AGCACGAAAA CGGCACAGAT CCCCGGGACA CCAACGAATG CCGCGCCACC    600

GAGTTCGCTG TGCGCTCTGG GCTGCTCACC GTCATGGTGT GGGTGTCCAG CGTCTTCTTC    660

TTTCTACCGG TCTTCTGCCT CACTGTGCTC TACAGTCTCA TCGGGAGGAA GCTATGGCGG    720

AGACGCGGAG ATGCAGCGGT GGGCGCCTCG CTCCGGGACC AGAACCACAA GCAGACAGTG    780

AAGATGCTTG TGAGTCCTG GCACCCGCTG ACCTTTCTTC CCCCACTGCC TGCCCTTCCC    840

CAGCGGCCTC TATTTCTGTT TCTCATCATC TCCGCTCCCC AAGTCTCTCA AGTCTCTGTC    900

TTTCTCTGCC TCTCTCACCT TGGTTCTCGG TCTCACTGCT TTCTGTTTTC TTCCTGTCTT    960

TTCCTGTATC TTGTCCACGA AAAGAACCCC TCATATTGGT AATTCCTTAA AACGAGGAAC    1020

CTTGGTCTGG GAAAATTGGT CCAAGATGGA AATACCTCAC GGTTTATTGA GCCCCTAATT    1080

GTTAACGGTT TAGCTTCTTG TCTCACATAG AATTTGTGGT TATCAAAGTA ATAATATTAA    1140

GGTAAGCAGG CAGGTAATGG GTTTAGAAAT CACTCCATGG TAAGTCTAAC CACAAATTTG    1200

GGTCACTCTG TTAAGGACGG CTTATAGATG TATTTTGTTT GTTTTCAATA TTGGGATTTG    1260

TTTTCTGCCC TGCATCTTTC TCAGATAATT ACATCCACTC TGTTTAGTCT ATGGTTTTGC    1320

CAGGAGGGGC TTCATGCTGG GGTCTCCTTT TTCTTGTTTT TGTATTTGTC TCCCCAGTAA    1380

TATAGGCCAG GATAGGGTGG AGAAGTCATC CTTTCCTCAA ACTGTCCTTC AGGAAGGTCT    1440

GGGTACTGAA CGGTTACTGC ATAAACTCTG CTTCCCCAAA GGCATGTGCT TGGTGTGGTA    1500

AAGTCATGAA GATGGTGCTC ATGTCCAAGA GGAACCTCTG ATCTCACTTT TCAAGGGATT    1560

TCATGTTTGC TGACATTTAA TACTTGTTAG TTTTTGCAGG GGGATGATTT CTCATTTGCA    1620

ATTTTATTAT TCTCAAATTC TGCATGTCAG AATGTTAGAG ATTTCTCAGG GATGTCAGGT    1680

TCTGTTTCCA GATGAGTGAT TGCCCTGTGT CCTCCATTGG ACTGTAAACT CATATGCACC    1740

AGACAGGGTC TACATTGCTG CCGTGGTGCA TAGCCTTCCA TGTGTCACTT AGTCCTAAAG    1800

AGAAGTTACT AATAACCTAA TCTCACTAAT CTCACTGGCA TCTCAATGCC GATCCCATTG    1860

TCATCTGAAA ATTTGAAGGG GACATTAAAG TGGCACAGGG ACCAGAACAA TATTTTTCTC    1920

TCATTGCTGA ATTTTAAAAA CAATCTAAAA AATTGGAATT CTTGAAGAAA CTATCTTATA    1980

TGACTAAAAT GAAGCCTTGG GTGGGTGCTA ATTATTATTG TCTGGCTTAC CTGCCCCCCC    2040

CACTACTTAT ATCTTTTAGA GATGCACAG ACTTGCTTTC CCTGTGGCTA CTAATCCCAA    2100

TTGCACATTC AGTCCCTTGA TAGACTTACT CTAAAAATCT AAGTTCAGCG GTCCACGAAA    2160

CATAACAAAG CCTGTCCTAA AACAGAAAGA AAGAAAGAAA GAAAGAAAGA AAGAAAGAAA    2220

GAAAGAAAGA AAGAAAGAAA ACAGAAGACA AACAAGGTCT TTCCCCATTC CCTAACATAC    2280

AGGAATGGAA ATTATTAAGT CTACGTGATA GCCAATGAAT CTGTTTCTTA AGTATGCCCA    2340

CAAGGGTGCT GCCGGAGCCA TTGCTCAGGG CTGGAGTATT TACTGGGCAT GCTTGACCCC    2400

AGCATGGAGG GTGAGAAGTG CTCCTGGGAA CTCTGATCCA CTGCTGTGGT GGAGAGCAAA    2460

CACCTGGCCT CATTTATACT TGTTGTCTGT ATAATGCATA TAAATGGGGG ATAATCATTA    2520

CTAAACTGTT TAGCTGAGCC TCATGTCAGT CAATCACAAA GCAGAGTAAT TACCACACAG    2580
```

```
ACTGGGAAGC TCAGTGAAGA TTGTTAGCGG TTGGTCTGAC AGTCTTGCTG TGTGCTATAG    2640

TGTTAGACCC AACGGAGGCA GTATTTATAA GGAGGGCAGG GTTCCATGTT TCCCGTGTTA    2700

AAGAGCAAGA GATGATGTTT GTCAGTAGGC ATGCAGCTCA TGGTGAAAAG AAAGTCCAGA    2760

CTTAAAGATG TGAAGTGATT TGTGCTTTGC CCCACCCTGA CAGTCTCTCT CTGTGTGCCT    2820

TCAGCTGTGG TGGTGTTTGC TTTCATCCTC TGCTGGCTGC CCTTCCACGT GGGAAGATAC    2880

CTCTTTTCCA AGTCCTTCGA GCCTGGCTCT CTGGAGATCG CTCAGATCAG CCAGTACTGC    2940

AACCTGGTGT CCTTTGTCCT CTTCTACCTC AGCGCTGCCA TCAACCCCAT TCTGTACAAC    3000

ATCATGTCCA AGAAGTACCG GGTGGCAGTG TTCAAACTGC TAGGATTTGA ATCCTTCTCC    3060

CAGAGAAAGC TTTCCACTCT GAAGGATGAG AGTTCCCGGG CCTGGACAAA GTCGAGCATC    3120

AACACATGA                                                            3129
```

(2) INFORMATION FOR SEQ ID NO: 15:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
ATGTGGAACG CGACCCCCAG CGAGGAGCCG GAGCCTAACG TCACGTTGGA CCTGGATTGG      60

GACGCTTCCC CCGGCAACGA CTCACTGCCT GACGAACTGC TGCCGCTGTT CCCCGCTCCG     120

CTGCTGGCAG GCGTCACCGC CACCTGCGTG GCGCTCTTCG TGGTGGGCAT CTCAGGCAAC     180

CTGCTCACTA TGCTGGTGGT GTCCCGCTTC CGCGAGCTGC GCACCACCAC CAACCTCTAC     240

CTGTCCAGCA TGGCCTTCTC GGATCTGCTC ATCTTCCTGT GCATGCCGCT GGACCTCGTC     300

CGCCTCTGGC AGTACCGGCC CTGGAACTTC GGCGACCTGC TCTGCAAACT CTTCCAGTTT     360

GTCAGCGAGA GCTGCACCTA CGCCACGGTC CTCACCATCA CCGCGCTGAG CGTCGAGCGC     420

TACTTCGCCA TCTGCTTCCC TCTGCGGGCC AAGGTGGTGG TCACTAAGGG CCGCGTGAAG     480

CTGGTCATCC TTGTCATCTG GGCCGTGGCT TTCTGCAGCG CGGGGCCCAT CTTCGTGCTG     540

GTGGGCGTGG AGCACGAAAA CGGCACAGAT CCCCGGGACA CCAACGAATG CCGCGCCACC     600

GAGTTCGCTG TGCGCTCTGG GCTGCTCACC GTCATGGTGT GGGTGTCCAG CGTCTTCTTC     660

TTTCTACCGG TCTTCTGCCT CACTGTGCTC TACAGTCTCA TCGGGAGGAA GCTATGGCGG     720

AGACGCGGAG ATGCAGCGGT GGGCGCCTCG CTCCGGGACC AGAACCACAA GCAGACAGTG     780

AAGATGCTTG CTGTGGTGGT GTTTGCTTTC ATCCTCTGCT GGCTGCCCTT CCACGTGGGA     840

AGATACCTCT TTTCCAAGTC CTTCGAGCCT GGCTCTCTGG AGATCGCTCA GATCAGCCAG     900

TACTGCAACC TGGTGTCCTT TGTCCTCTTC TACCTCAGCG CTGCCATCAA CCCCATTCTG     960

TACAACATCA TGTCCAAGAA GTACCGGGTG GCAGTGTTCA AACTGCTAGG ATTTGAATCC    1020

TTCTCCCAGA GAAAGCTTTC CACTCTGAAG GATGAGAGTT CCCGGGCCTG GACAAAGTCG    1080

AGCATCAACA CA                                                        1092
```

(2) INFORMATION FOR SEQ ID NO: 16:

(i) SEQUENCE CHARACTERISTICS:
        (A) LENGTH: 364 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO: 16:

```
Met Trp Asn Ala Thr Pro Ser Glu Glu Pro Glu Asn Val Thr Leu
 1               5                  10                  15

Asp Leu Asp Trp Asp Ala Ser Pro Gly Asn Asp Ser Leu Pro Asp Glu
            20                  25                  30

Leu Leu Pro Leu Phe Pro Ala Pro Leu Leu Ala Gly Val Thr Ala Thr
            35                  40                  45

Cys Val Ala Leu Phe Val Val Gly Ile Ser Gly Asn Leu Leu Thr Met
 50                  55                  60

Leu Val Val Ser Arg Phe Arg Glu Leu Arg Thr Thr Thr Asn Leu Tyr
 65                  70                  75                  80

Leu Ser Ser Met Ala Phe Ser Asp Leu Leu Ile Phe Leu Cys Met Pro
            85                  90                  95

Leu Asp Leu Val Arg Leu Trp Gln Tyr Arg Pro Trp Asn Phe Gly Asp
            100                 105                 110

Leu Leu Cys Lys Leu Phe Gln Phe Val Ser Glu Ser Cys Thr Tyr Ala
            115                 120                 125

Thr Val Leu Thr Ile Thr Ala Leu Ser Val Glu Arg Tyr Phe Ala Ile
            130                 135                 140

Cys Phe Pro Leu Arg Ala Lys Val Val Val Thr Lys Gly Arg Val Lys
145                 150                 155                 160

Leu Val Ile Leu Val Ile Trp Ala Val Ala Phe Cys Ser Ala Gly Pro
                165                 170                 175

Ile Phe Val Leu Val Gly Val Glu His Glu Asn Gly Thr Asp Pro Arg
                180                 185                 190

Asp Thr Asn Glu Cys Arg Ala Thr Glu Phe Ala Val Arg Ser Gly Leu
            195                 200                 205

Leu Thr Val Met Val Trp Val Ser Ser Val Phe Phe Leu Pro Val
            210                 215                 220

Phe Cys Leu Thr Val Leu Tyr Ser Leu Ile Gly Arg Lys Leu Trp Arg
225                 230                 235                 240

Arg Arg Gly Asp Ala Ala Val Gly Ala Ser Leu Arg Asp Gln Asn His
                245                 250                 255

Lys Gln Thr Val Lys Met Leu Ala Val Val Phe Ala Phe Ile Leu
            260                 265                 270

Cys Trp Leu Pro Phe His Val Gly Arg Tyr Leu Phe Ser Lys Ser Phe
            275                 280                 285

Glu Pro Gly Ser Leu Glu Ile Ala Gln Ile Ser Gln Tyr Cys Asn Leu
            290                 295                 300

Val Ser Phe Val Leu Phe Tyr Leu Ser Ala Ala Ile Asn Pro Ile Leu
305                 310                 315                 320

Tyr Asn Ile Met Ser Lys Lys Tyr Arg Val Ala Val Phe Lys Leu Leu
                325                 330                 335

Gly Phe Glu Ser Phe Ser Gln Arg Lys Leu Ser Thr Leu Lys Asp Glu
            340                 345                 350

Ser Ser Arg Ala Trp Thr Lys Ser Ser Ile Asn Thr
            355                 360
```

What is claimed is:

1. A method to determine the presence of a growth hormone secretagogue receptor ligand comprising:
   a) introducing a nucleic acid which encodes a growth hormone secretagogue receptor (GHSR) into a cell under conditions so that said growth hormone secretagogue receptor is expressed:
   b) introducing a detector molecule or a nucleic acid encoding a detector molecule into the cell, wherein the detector molecule is directly or indirectly responsive to a GHSR-ligand binding event;
   c) contacting the cell with a compound suspected of being a growth hormone secretagogue receptor ligand; and
   d) determining whether the compound is a growth hormone secretagogue receptor ligand by detecting a response of the detector molecule, wherein a response of the detector molecule indicates the presence of a GHSR-ligand.

2. An assay method to determine the presence of a growth hormone secretagogue receptor ligand comprising:
   a) introducing a nucleic acid which encodes a growth hormone secretagogue receptor (GHSR) into a cell under conditions so that said growth hormone secretagogue receptor is expressed:
   b) introducing a G-protein subunit or a nucleic acid encoding a G-protein subunit into the cell;
   c) introducing a detector molecule or a nucleic acid encoding a detector molecule into the cell, wherein the detector molecule is directly or indirectly responsive to a GHSR-ligand binding event;
   d) contacting the cell with a compound suspected of being a growth hormone secretagogue receptor ligand; and
   e) determining whether the compound is a growth hormone secretagogue receptor ligand by detecting a response of the detector molecule, wherein a response of the detector molecule indicates the presence of a GHSR-ligand.

3. A method according to claim 2 wherein the G protein subunit is a G-alpha subunit.

4. A method according to claim 3 wherein the G-protein subunit is the $G_{\alpha 11}$ subunit.

5. A method according to claim 2 further comprising comparing the result of step e) to that obtained using a known growth hormone secretagogue receptor ligand.

6. An assay for identifying a ligand which binds to a human growth hormone secretagogue receptor, wherein said receptor is expressed in a host cell which does not naturally express human GHSR, comprising contacting a putative ligand with a human growth hormone secretagogue receptor in the presence of a G protein subunit α11 and determining whether binding has occurred, wherein binding indicates the presence of a ligand which binds to human GHSR.

7. An assay according to claim 6 wherein binding is detected by a response of a detector molecule.

8. An assay according to claim 7 wherein the detector molecule is aequorin.

* * * * *